US012594090B2

(12) United States Patent
Korman

(10) Patent No.: US 12,594,090 B2
(45) Date of Patent: Apr. 7, 2026

(54) MINIMALLY INVASIVE SURGERY INFLOW CANNULA DEVICE

(71) Applicant: WRIGHT MEDICAL TECHNOLOGY, INC., Memphis, TN (US)

(72) Inventor: Zachary Korman, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 861 days.

(21) Appl. No.: 17/704,608

(22) Filed: Mar. 25, 2022

(65) Prior Publication Data

US 2022/0313301 A1 Oct. 6, 2022

Related U.S. Application Data

(60) Provisional application No. 63/168,396, filed on Mar. 31, 2021.

(51) Int. Cl.
*A61B 17/32* (2006.01)
*A61B 17/00* (2006.01)

(52) U.S. Cl.
CPC .. *A61B 17/32002* (2013.01); *A61B 17/00234* (2013.01); *A61B 2217/007* (2013.01); *A61B 2218/002* (2013.01)

(58) Field of Classification Search
CPC ........ A61B 17/32002; A61B 2217/007; A61B 2218/002; A61B 2217/005; A61B 2218/001; A61B 17/3417; A61B 2017/348–3492; A61B 2018/00291; A61B 2017/32007; A61B 2017/22079;
(Continued)

(56) References Cited

U.S. PATENT DOCUMENTS 5,947,990 A * 9/1999 Smith .............. A61B 17/32002
606/180
10,413,305 B2 9/2019 Magno et al.
(Continued)

OTHER PUBLICATIONS

"Cannulas", https://www.conmed.com/en/products/orthopedics/aed/fluid-management/tubing/cannulasm, Conmed, accessed on Mar. 15, 2022, 5 pages.
(Continued)

*Primary Examiner* — Elizabeth Houston
*Assistant Examiner* — Daniel Icet
(74) *Attorney, Agent, or Firm* — DUANE MORRIS LLP

(57) ABSTRACT

Irrigation systems and methods are disclosed. An irrigation system includes a body defining a proximal portion and a distal portion. The proximal portion defines a cavity sized and configured to receive a working end of a hand-piece therein. An inlet tube extends through a portion of the body and is configured to receive a fluid flow therethrough. An outlet tube assembly is coupled to the distal portion of the body and extends distally beyond a distal edge of the body. The outlet tube assembly includes an inner tube and an outer tube. The inner tube and the outer tube define a fluid path therebetween. The inlet tube is in fluid communication with the outlet tube assembly such that the fluid flow received through the inlet tube flows through the fluid path of the outlet tube assembly and exits the outlet tube assembly at a distal end.

18 Claims, 17 Drawing Sheets

(58) Field of Classification Search
CPC ........ A61B 2017/320084; A61M 1/71; A61M
1/76; A61M 1/77; A61M 1/774
See application file for complete search history.

(56) References Cited

U.S. PATENT DOCUMENTS

| | | | |
|---|---|---|---|
| 2003/0153926 A1* | 8/2003 | Schmieding ....... | A61B 17/3421 |
| | | | 606/108 |
| 2005/0203342 A1* | 9/2005 | Kucklick .......... | A61B 1/00094 |
| | | | 600/156 |
| 2009/0270894 A1 | 10/2009 | Rubin et al. | |
| 2011/0152773 A1* | 6/2011 | McCawley ........ | A61B 17/3421 |
| | | | 604/164.01 |
| 2012/0029354 A1 | 2/2012 | Mark et al. | |
| 2018/0206883 A1* | 7/2018 | McIntyre ........... | A61B 17/3423 |
| 2019/0099202 A1* | 4/2019 | Morgan ............. | A61B 17/3417 |
| 2019/0262006 A1* | 8/2019 | Schwamb ........ | A61B 17/32002 |

OTHER PUBLICATIONS

"Arthrex Cannulas", https://www.arthrex.com/search?q=cannula, accessed on Mar. 15, 2022, accessed on Mar. 15, 2022, 8 pages.
"Smith & Nephew Cannulas" https://www.smith-nephew.com/professional/products/sports-medicine1/access/cannulas/, accessed on Mar. 15, 2022.
"Dri-Lok Disposable Cannulas", https://www.stryker.com/content/dam/stryker/sports-medicine/products/dri-lokcannula/resources/Dri-Lok%20Cannula%20Brochure.pdf, 3 pages, 2006.
Extended European Search Report in connection with corresponding Patent Application No. 22165426.2, Jul. 29, 2022, 7 pages.

* cited by examiner

300

Couple Irrigation System to Hand Piece
302

Couple Irrigation System to Irrigation Source
304

Deliver Irrigation Fluid via Outlet
Tube Assembly
306

Perform Additional Surgical Procedure
308

MINIMALLY INVASIVE SURGERY INFLOW CANNULA DEVICE

CROSS-REFERENCE TO RELATED APPLICATION

This application claims priority to U.S. Provisional Patent Application No. 63/168,396, filed Mar. 31, 2021, the entirety of which is incorporated by reference herein.

TECHNICAL FILED

This application relates generally to minimally invasive surgery (MIS) systems, and, more specifically, MIS irrigation systems.

BACKGROUND

Minimally invasive surgery ("MIS") is an alternative to traditional, open surgery. MIS generally results in less pain and shorter hospital stays for the patient and reduces the cost of performing a surgical procedure. In MIS, the operation is carried out through a small incision. MIS procedures may reduce trauma to the patient's muscles and other tissues, and typically result in shorter patient recovery time. However, operating in the confines of a small incision presents challenges to the surgeon. The surgeon must often rely on specialized surgical instruments in order to access or operate within the surgical site.

During surgery, it may be necessary to deliver a fluid, such as a medicinal, cooling, and/or lubricating fluid, to a working site. Fluid delivery may be provided to reduce friction between a tool and a working site, apply one or more medicinal compounds to a working site, reduce heat generation from the use of tools, for cleaning and/or removal of debris, and/or any other suitable purpose. The use of irrigation systems in MIS surgery is complicated by the use of small incisions and the low visibility or access to a working site.

SUMMARY

In various embodiments, a system is disclosed. The system includes a body defining a proximal portion and a distal portion. The proximal portion defines a cavity sized and configured to receive a working end of a hand-piece therein. An inlet tube extends through a portion of the body and is configured to receive a fluid flow therethrough. An outlet tube assembly is coupled to the distal portion of the body and extends distally beyond a distal edge of the body. The outlet tube assembly comprises an inner tube and an outer tube. The inner tube and the outer tube define a fluid path therebetween. The inlet tube is in fluid communication with the outlet tube assembly such that the fluid flow received through the inlet tube flows through the fluid path of the outlet tube assembly and exits the outlet tube assembly at a distal end.

In various embodiments, a system is disclosed. The system includes a powered hand-piece comprising a working end, a cutting tool operatively coupled to the working end of the powered hand-piece, and an irrigation system coupled to the working end of the powered hand-piece. The irrigation system includes a body defining a proximal portion and a distal portion. The proximal portion defines a cavity sized and configured to receive a working end of a hand-piece therein and the distal portion defines a tool channel sized and configured to receive the cutting tool therethrough. An inlet tube extends through a portion of the body and is configured to receive a fluid flow therethrough. An outlet tube assembly is coupled to the distal portion of the body and extends at least partially through the tool channel. The outlet tube assembly includes an inner tube and an outer tube defining a fluid path therebetween. The inlet tube is in fluid communication with the outlet tube assembly such that the fluid flow received through the inlet tube flows through the fluid path of the outlet tube assembly and exits the outlet tube assembly at a distal end. The distal end of the outlet tube assembly provides the fluid circumferentially about the tool.

In various embodiments, a method is disclosed. The method includes a step of coupling an irrigation system to a powered hand-piece. The irrigation system includes a body defining a proximal portion and a distal portion. The proximal portion defines a cavity sized and configured to receive a working end of the hand-piece therein. An inlet tube extends through a portion of the body and an outlet tube assembly is coupled to the distal portion of the body. The outlet tube assembly extends at least partially through the tool channel. The outlet tube assembly includes an inner tube and an outer tube defining a fluid path therebetween. The inlet tube is in fluid communication with the outlet tube assembly. The method further includes a step of coupling a cutting tool to the powered hand-piece. The cutting tool is received through a tool channel defined in the distal portion of the body. The method further includes a step of providing fluid flow to a distal end of the tool. The fluid flow is provided through the inlet tube and the fluid path of the outlet tube assembly. The distal end of the outlet tube assembly provides the fluid circumferentially about the tool.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
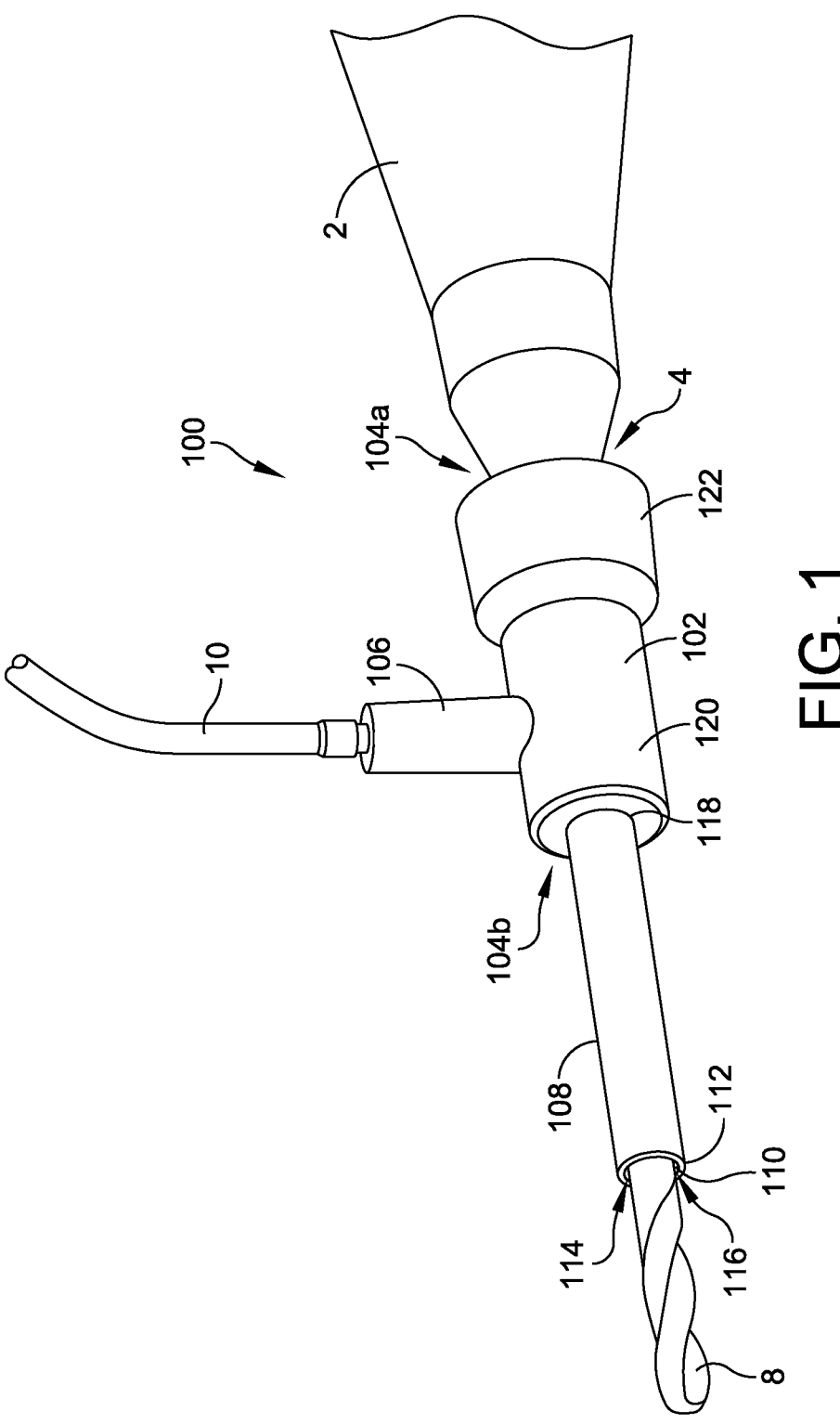
FIG. 1 illustrates an irrigation system coupled to a powered hand-piece, in accordance with some embodiments.

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

In various embodiments, a method and system for irrigating a surgical site during application of a powered hand tool is disclosed. In some embodiments, an irrigation system includes an irrigation body configured to be coupled to a working end of a powered hand piece (e.g., a powered hand tool such as a drill, impact driver, etc.). The irrigation body includes an inlet configured to be coupled to tubing, such as, for example, irrigation tubing of an external irrigation system. The body further defines a tool passage having a first, inner tube and a second, outer tube each defining a channel positioned circumferentially with the tool passage. The inner tube and the outer tube define a fluid passage therebetween. The fluid passage is in fluid communication with the inlet.

FIG. 1 illustrates an irrigation system 100 coupled to a powered hand-piece 2, in accordance with some embodiments. The irrigation system 100 includes a body 102 configured to be coupled to a distal, or working, end 4 of the powered hand-piece 2. For example, in some embodiments, the proximal end 104*a* of the body 102 defines an opening sized and configured to be slideably coupled to the working end 4 of the hand-piece 2 (see FIG. 2). The body 102 may be coupled to the hand-piece 2 using any suitable coupling mechanism, such as, for example, a press-fit (e.g., a pinwheel coupling element, an interference bump, etc.), an adhesive, screws, pins, and/or any other suitable coupling mechanism. In some embodiments, the body 102 is formed integrally with and/or fixedly coupled to the distal end of the powered hand-piece 2.

The body 102 includes an inlet path 106. The inlet path 106 is sized and configured to be coupled to an irrigation tube 10. The irrigation tube 10 may be part of an external irrigation source and/or an irrigation source formed integrally with the powered hand tool 2. The irrigation tube 10 may be slideably or otherwise releasably coupled to the inlet path 106 of the body 102 or may be formed integrally with or otherwise permanently coupled to the inlet path 106 of the body 102. The irrigation tube 10 is configured to deliver a fluid, such as an irrigation and/or medicinal fluid, from the irrigation source to the inlet 106.

In some embodiments, the irrigation system 100 includes an outlet tube assembly 108 extending from a distal end 104*b* of the body 102. The outlet tube assembly 108 includes at least a first, inner tube 110 and a second outer tube 112. The inner tube 110 and the outer tube 112 define a fluid passage 114 therebetween (see FIG. 2). The inner tube 110 defines a tool passage 116 sized and configured to receive a tool 8 therethrough. The tool 8 is configured to extend through the body 102 and couple to the working end 4 of the powered hand-piece 2, for example, extending from the proximal end 104*a* of the body 102 beyond the distal end 104*a*. In some embodiments, the tool 8 includes a bit, such as a drill bit, driving bit, burr bit, router bit, mill bit, reamer bit, etc. operatively coupled to the powered hand-piece 4.

Figure 2:
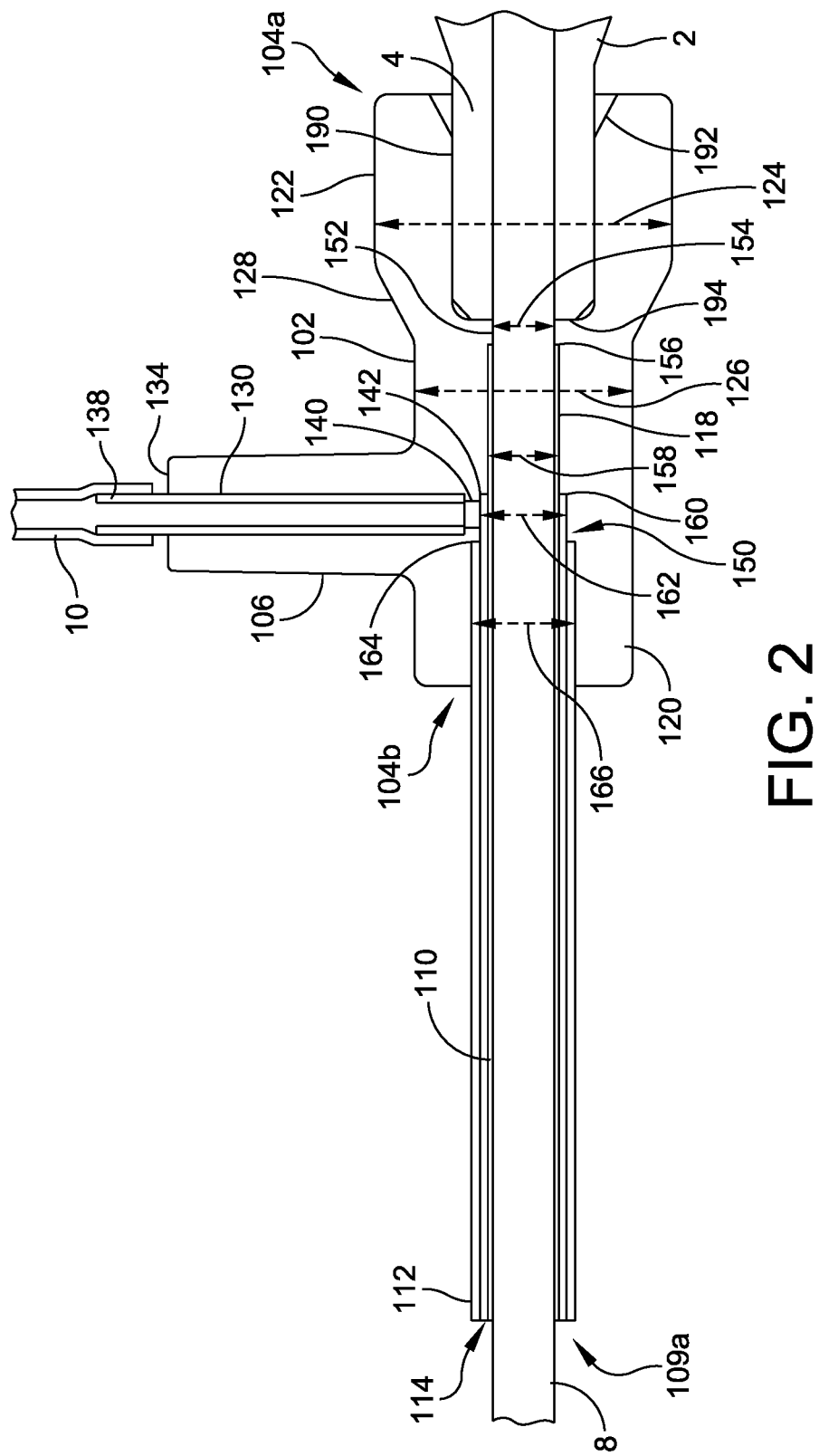
FIG. 2 illustrates a cross-sectional view of the irrigation system of FIG. 1, in accordance with some embodiments.

The outlet tube assembly 108 may be releasably and/or permanently coupled to the body 102. For example, in some embodiments, the outlet tube assembly 108 is received within a circumferential channel 118 defined by a distal portion 120 of the body 102, as shown in FIG. 2. The circumferential channel 118 may be centered in the distal portion 120 of the body (as illustrated) and/or offset from the center of the distal portion 120. The outlet tube assembly 108 may be coupled within the circumferential channel 118 by a press-fit (e.g., a pinwheel coupling element, an interference bump, etc.), adhesive, and/or other releasable coupling mechanism. In other embodiments, the outlet tube assembly 108 may be formed integrally with and/or permanently coupled to the body 102. For example, the outlet tube assembly 108 may be coupled to the body 102 by a laser weld, adhesive, and/or other permanent coupling mechanism.

In the illustrated embodiment, the body 102 includes a continuous material defining each of the inlet 106, the distal portion 120, and a proximal portion 122, although it will be appreciated that one or more portions of the body 102 may be formed separately and coupled together. The proximal portion 122 defines a first diameter 124 and the distal portion 120 defines a second diameter 126. The first diameter 124 may be greater than the second diameter 126 (as shown in FIG. 1), less than the second diameter 126, and/or equal to the second diameter 126. In some embodiments, the proximal portion 122 may be coupled to the distal portion 124 by a tapered section 128. The taper may be selected to be any suitable angle and may extend over any suitable length to transition from the proximal portion 122 to the distal portion 120.

In some embodiments, the inlet 106 is formed integrally with the distal portion 120. The inlet 106 may be positioned at any suitable angle with respect to the distal portion 120 and/or the circumferential channel 118 defined by the distal portion 120 of the body 102. In the illustrated embodiment, the inlet 106 is formed perpendicular to the distal portion 120 and the internal passage of the inlet 106 extends substantially along an axis positioned perpendicular to an axis defined by the circumferential channel 118 of the distal portion 120. Although embodiments are discussed herein including a perpendicular arrangement between the inlet 106 and the distal portion 120, it will be appreciated that the inlet 106 may be positioned at any suitable angle with respect to the distal portion 120. For example, in some embodiments, the inlet 106 may be positioned at any angle between 0° (e.g., parallel with and/or formed integrally with the distal portion 120) and 90° (perpendicular with the distal portion 120).

In operation, an irrigation fluid is provided from the irrigation source to the inlet 106 via the irrigation tube 10. The inlet 106 is in fluid communication with the fluid passage 114 defined between the inner tube 110 and the outer tube 112 of the outlet tube assembly 108. Irrigation fluid flows from the irrigation source, through the irrigation system 100, and is provided to a distal end 109*a* of the outlet tube assembly 108. The irrigation fluid is provided to a surgical site simultaneously with application of the tool 8. The circumferential fluid passage 114 directs the irrigation fluid to the surgical site such that irrigation fluid may be provided circumferentially around the tool 8, which ensures that irrigation fluid is provided to the entirety of the surgical site as needed during application of the tool 8.

The fluid passage 114 eliminates the need for sealing components, flutes, or other irrigation measures to direct the full stream of irrigation fluid to the surgical site. The fluid passage 114, unlike conventional irrigation systems, provides only a single path for the irrigation fluid to the surgical site and provides circumferential flow of the irrigation fluid about the surgical site. The use of sealing mechanisms required in traditional irrigation systems is eliminated, as the irrigation flow has no other possible path that would require sealing to negate. Instead, only a single path, directed at the working end of a tool 8, is provided.

FIG. 2 illustrates a cross-sectional view of the irrigation system 100 of FIG. 1, in accordance with some embodiments. As shown in FIG. 2, the inlet path 106 includes an inlet tube 130. The inlet tube 130 may comprise a cannula or other fluid passage coupled to and/or embedded within the body 102 and/or may be defined by a portion of the body 102. In the illustrated embodiment, a portion of the inlet tube 130 extends beyond an upper edge 134 of the body 102 to define a mating end 138 configured to be coupled to the irrigation tube 10. The inlet tube 130 and the irrigation tube 10 may be coupled using any suitable coupling mechanism, such as, for example, a press-fit engagement, adhesive, threaded engagement, a pin mechanism, formed integrally together, and/or any other suitable coupling mechanism. Although embodiments are illustrated with an inlet tube 130 coupled to a separate irrigation tube 10, it will be appreciated that the inlet tube 130 and the irrigation tube 10 may be formed of a single continuous cannula coupled to and/or formed integrally with the body 102 and extending to the separate irrigation source (not shown).

A fluid path defined by the inlet tube 130 is in fluid communication with the fluid path 114 defined by the outlet tube assembly 108. The inlet tube 130 may be coupled directly to the outlet tube assembly 108 and/or may be coupled by one or more fluid passages 140 defined by the body 102. In embodiments having the inlet tube 130 coupled directly to the outlet tube assembly 108, the inlet tube 130 may be fixedly coupled to the outlet tube assembly 108, formed integrally with the outlet tube assembly 108, releasably coupled to the outlet tube assembly 108, and/or positioned in an abutting relationship with the outlet tube assembly 108. Similarly, in embodiments in which the inlet tube 130 is coupled to the outlet tube assembly 108 by one or more additional fluid passages 140, the inlet tube 130 and/or the outlet tube assembly 108 may each be fixedly coupled to one or more additional fluid passages, formed integrally with the one or more additional fluid passages 140, releasably coupled to the one or more additional fluid passages 140, and/or positioned in an abutting relationship with one or more additional fluid passages 140.

In some embodiments, the inlet tube 130, the outlet tube assembly 108, and, if present, the one or more additional fluid passages 140 define a continuous fluid path from the irrigation tube 10 to the distal end 109*a* of the outlet tube assembly 108. The continuous fluid path allows irrigation fluid to be delivered from the irrigation source (not shown) to the surgical site circumferentially about a working end of a tool 8. As discussed above with respect to FIG. 1, the continuous fluid path eliminates the need for additional sealing and/or fluid directing mechanisms, such as seals or flutes, and provides a direct flow of irrigation fluid to a surgical site during operation of a tool 8.

The fluid path defined by the inlet tube 130 is coupled to the fluid passage 114 defined between the inner tube 110 and the outer tube 112 of the outlet tube assembly 108 such that a fluid flow 141*a* (see FIG. 3) through the inlet tube 130 is provided circumferentially 141*b* about the inner tube 110 and flows distally 141*c* prior to exiting the distal end 109*a* of the outlet tube assembly 108. In some embodiments, the fluid path of the inlet tube 130 is coupled directly to the fluid passage 114 through a portion of the outer tube 112 of the outlet tube assembly 108 (see FIG. 4).

Figure 3:
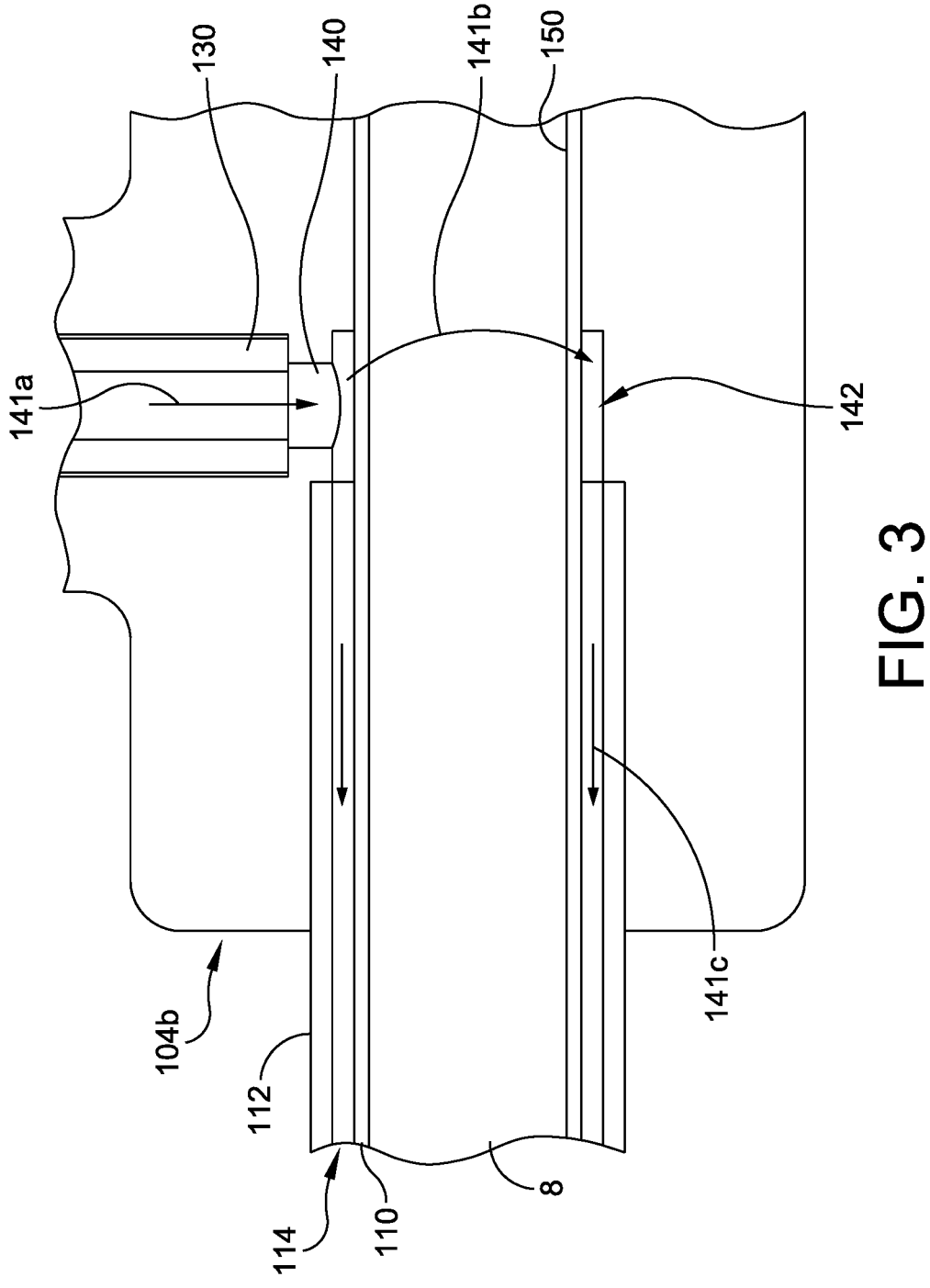
FIG. 3 illustrates a close-up view of a tube connection of the irrigation system of FIG. 1 including a press fit connection for an inner tube, in accordance with some embodiments.

As illustrated in FIG. 3, in some embodiments, the outer tube 112 terminates proximal to the to the position of the inlet tube 130 such that the fluid passage 114 is exposed distally of the inlet tube 130 to allow fluid to flow from the inlet tube 130, over the inner tube 112, and through the fluid passage 114. As illustrated in FIG. 2, the inlet tube 130 is coupled to an internal fluid path 140 defined by the body 102. Fluid flows through the inlet tube 130 and into the internal fluid path 140. The internal fluid passage 140 is coupled to a circumferential cavity 142 defined by the body 102 and the inner tube 110 of the outlet tube assembly 108. The circumferential cavity 142 is in fluid communication with the fluid passage 114 of the outlet tube assembly 108 such that irrigation fluid flowing into the circumferential cavity 142 is forced into the fluid passage 114 and travels distally. As shown in FIG. 2, the outer tube 112 of the outlet tube assembly 108 terminates distally of the circumferential cavity 142 while the inner tube 110 extends proximally beyond the circumferential cavity 142, providing a fluid-tight seal in the proximal direction while allowing flow of the irrigation fluid in the distal direction. Although embodiments are illustrated herein including an outer tube 112 terminating distally of an inner tube 110, it will be appreciated that the outer tube 112 may extend proximally the same distance and/or a greater distance than the inner tube 110. In such embodiments, the fluid path of the inlet tube 130 is coupled to the fluid passage 114, for example, by passing through the outer tube 112 of the outlet tube assembly 108.

Referring again to FIG. 2, a distal end 109*a* of outlet tube assembly 108 is configured to direct a fluid flow from the fluid passage 114 circumferentially about a working end of a tool 8. In the illustrated embodiment, the inner tube 110 and the outer tube 112 terminate at the same distal position, although it will be appreciated that the outer tube 112 may extend further distally than the inner tube 110 in order to allow the irrigation fluid to interface with the tool 8 prior to termination of the fluid passage 114. In other embodiments, the inner tube 110 may extend further distally than the outer tube 112, allowing the irrigation fluid to disperse at the surgical site before contacting the tool 8.

As illustrated in FIG. 2, in some embodiments, the body 102 defines a continuous tool channel 150 extending from an internal circumferential wall 194 defined by the body 102 to a distal end 104*b* of the body 102. The tool channel 150 is sized and configured to receive a portion of the tool 8 therethrough. In some embodiments, the tool channel 150 is centered within the body 102, although it will be appreciated that the tool channel 150 may be offset within the body 102. In the illustrated embodiment, the tool channel 150 defines a circumferential channel extending through the body 102, although it will be appreciated that the tool channel 150 may include any suitable shape, such as, for example, any suitable geometric cross-section configured to receive a tool 108 therethrough.

In some embodiments, the tool channel 150 includes a stepped configuration to allow insertion of the outlet tube assembly 108 and/or portions of the outlet tube assembly 108, such as the inner tube 110 and/or the outer tube 112. For example, in the illustrated embodiment, the tool channel 150 includes a stepped configuration including a first portion 152 having a first diameter 154 extending from an internal circumferential wall 194 of the body to a first position 156. At the first position 156, the diameter of the tool channel 150 increases to a second diameter 158. The second diameter 158 is selected such that the inner tube 110 of the outlet tube assembly 108 and the tool 8 may be accommodated within the tool channel 150 without interfering with each other. For example, the inner tube 110 may define an internal diameter sufficient to accommodate the tool 8 therein such that the tool 8 does not contact the inner surface of the inner tube 110 and the second diameter may be selected to accommodate the inner tube 110 without applying compression to the inner tube 110 in order to maintain the internal diameter of the inner tube 110. In some embodiments, the inner tube 110 is formed at least partially of a rigid material configured to maintain the internal diameter even when a compression force is applied to the outer surface of the inner tube 110.

In some embodiments, the tool channel 150 includes a second portion extending from the first position 156 to a second position 160. The tool channel 150 increases to a third diameter 162 at the second position 160. The third diameter 162 increases a distance between the internal surface of the tool channel 150 and the outer surface of the inner tube 110 to define the circumferential cavity 142 discussed above. As discussed above, the circumferential cavity 142 is configured to receive irrigation fluid flow from the inlet path 106 and direct the irrigation fluid flow through the fluid passage 114 defined between the inner tube 110 and the outer tube 112 of the outlet tube assembly 108.

In some embodiments, the circumferential cavity 142 extends from the second position 160 to a third position 164, at which the tool channel 150 increases to a fourth diameter 166. The fourth diameter 166 is selected such that the outer tube 110 of the outlet tube assembly 108 may be inserted into the tool channel 150 without impinging on the fluid path 114 defined between the inner tube 110 and the outer tub 112. For example, the outer tube 112 may define an internal diameter sufficient to accommodate the inner tube 110 therein such that the inner tube 110 and the outer tube 112 define the fluid path 114 therebetween. The fourth diameter 166 may be selected to accommodate the outer tube 112 without applying compression to the outer tube 112 in order to maintain the internal diameter of the outer tube 112. In some embodiments, the outer tube 112 is formed at least partially of a rigid material configured to maintain the internal diameter even when a compression force is applied to the outer surface of the outer tube 112.

In some embodiments, the proximal portion 122 of the body 102 defines a head cavity 190 sized and configured to receive a head, or distal, portion 20 of a powered hand-piece 2 therein. The head cavity 190 may include an internal cavity having a perimeter equal to an outer perimeter of the head portion 20 of the powered hand-piece 2. For example, if the head portion 20 includes a circumferential cross-section having an outer diameter, the head cavity 190 may define a circumferential cross-section having an inner diameter substantially equal to the outer diameter of the head portion 20. It will be appreciated that the head portion 20 and/or the head cavity 190 may have any suitable cross-sectional shape configured to allow the head portion 20 to be inserted within the head cavity 190. For example, suitable geometric shapes may include circular, triangular, square, rectangular, hexagonal, octagonal, etc. Although specific examples are discussed herein, it will be appreciated that any suitable cross-sectional shape may be used.

In some embodiments, the head cavity 190 is sized and configured to provide a press-fit coupling with the head portion 20 of the powered hand-tool 2. For example, in some embodiments, the head cavity 190 may include an internal diameter substantially equal to, or slightly less than, an outer diameter of the head portion 20. When the head portion 20 is inserted into the head cavity 190, the inner surface of the head cavity 190 contacts the outer surface of the head portion 20 to provide a press-, or friction-, fit therebetween. In other embodiments, the body 102 may be coupled to the head portion 20 using any suitable coupling mechanism, such as, for example, a press-fit (e.g., a pinwheel coupling element, an interference bump, etc.), adhesive, thread, pin, set-screw, and/or any other suitable coupling mechanism. In still other embodiments, the body 102 may be formed integrally with and/or permanently coupled to the head portion 20 of the powered hand-piece 2.

In some embodiments, the head cavity 190 includes a proximal tapered region 192 configured to taper from a second diameter to the inner diameter of the head cavity 190. The proximal tapered region 192 is configured to guide the head portion 20 of the powered hand-piece 2 into alignment with the head cavity 190. In some embodiments, the proximal tapered region 192 may be configured to assist in guiding both the head portion 20 of the powered hand-piece 2 and a tool 8 into alignment with the body 102. Although embodiments are shown with a proximal tapered region 192, it will be appreciated that the proximal tapered region 192 may be omitted and the head cavity 190 may include a constant diameter extending from a proximal end to an internal circumferential wall 194.

Although specific embodiments are discussed herein, it will be appreciated that the internal structure of the body 102, for example the tool passage 150, may be defined using any suitable structures or configuration to accommodate a tool 8, inlet tube 130, outlet tube assembly 108, and/or other structures discussed herein. It will be appreciated that any of the structures discussed herein as separate structures may be formed integrally and/or permanently coupled together. Alternatively, it will be appreciate that any structures discussed herein as a monolithic structure may be divided into multiple interconnected parts.

Figure 4:
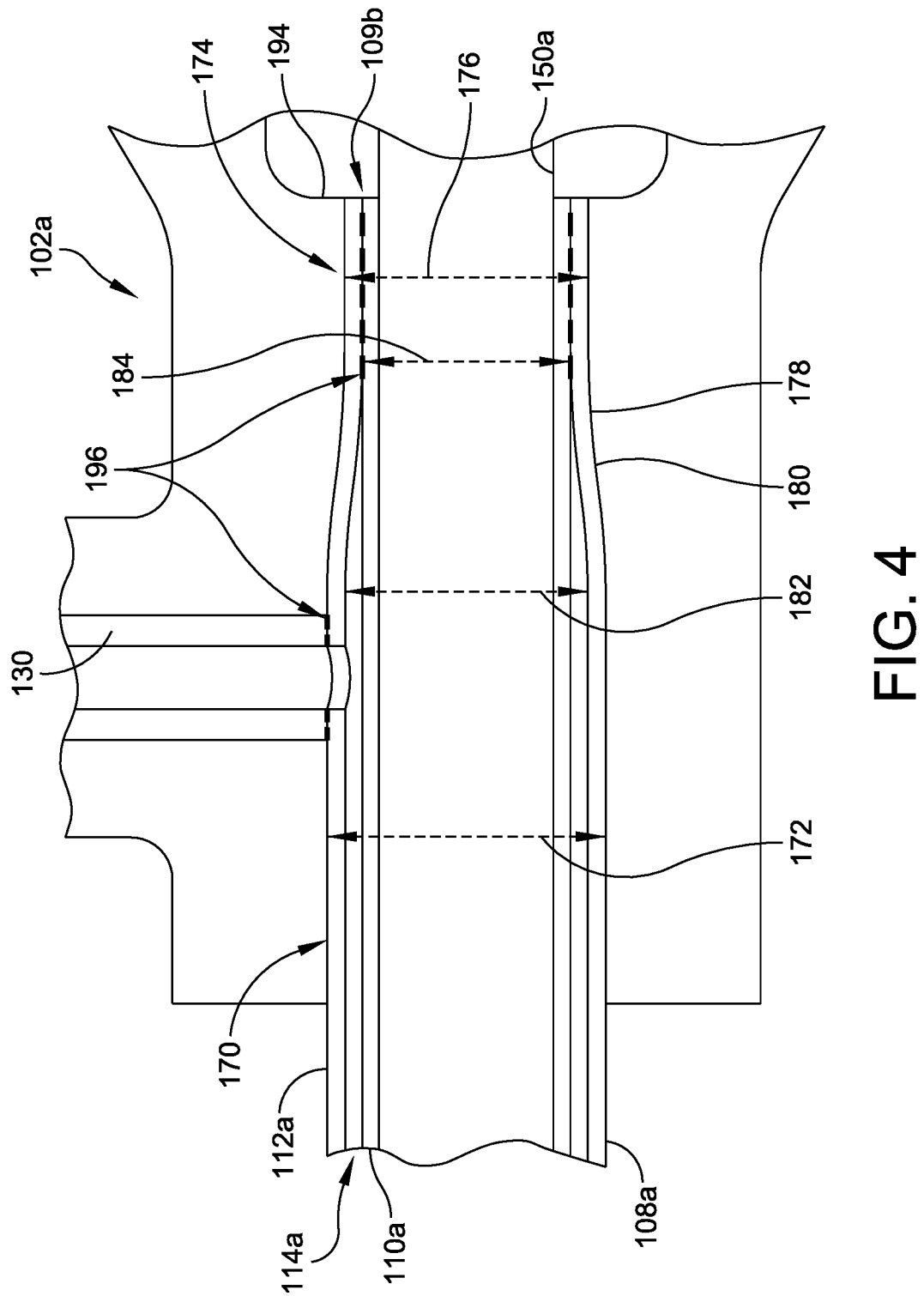
FIG. 4 illustrates a close-up view of a tube connection of the irrigation system of FIG. 1 including a laser weld connection for an inner tube, in accordance with some embodiments.

FIG. 4 illustrates a cross-sectional view of a body 102a having a sealed outlet tube assembly 108a inserted into a tool passage 150a defined therein, in accordance with some embodiments. The body 102a and the outlet tube assembly 108a are similar to the body 102 and outlet tube assembly 108 discussed above, and similar description is not repeated herein. The tool passage 150a defined by the body 102a includes a first circumferential portion 170 having a first diameter 172 and a second circumferential portion 174 having a second diameter 176. The first circumferential portion 170 and the second circumferential portion 174 are coupled by a tapered portion 178 that tapers from the first diameter 172 to the second diameter 176 over a predetermined longitudinal length.

The sealed outlet tube assembly 108a includes an inner tube 110a that is sealably coupled to the outer tube 112a at a proximal end to form a fluid-tight seal. The inner tube 110a may be coupled to the outer tube 112a using any suitable coupling mechanism, such as, for example, a laser-weld 196, although it will be appreciate that any suitable coupling mechanism, such as an ultrasonic weld, an adhesive, etc. may be used. The outer tube 112a may include a tapered section 180 extending from a first inner diameter 182 to a second inner diameter 184. In some embodiments, the second inner diameter 184 is less than the first inner diameter 182. The second inner diameter 184 may be substantially equal to the outer diameter of the inner tube 110a to facilitate welding of the inner tube 110a to the outer tube 112a.

In some embodiments, the inlet tube 130 is coupled to the outer tube 112a of the outlet tube assembly 108a such that a fluid path is defined through the outer tube 112a allowing fluid to pass from the internal channel 130 to the fluid passage 114a. In some embodiments, the inlet tube 130 may be coupled to the outer tube 112a using any suitable coupling mechanism, such as, for example, a laser-weld, an ultrasonic weld, an adhesive, etc., configured to provide a fluid tight seal.

In some embodiments, the outlet tube assembly 108a is configured to abut the circumferential wall 194 defined between the tool channel 150a and the head cavity 190 defined by a proximal portion 122 of the body 102a. The abutting relationship between the proximal end 109b of the outlet tube assembly 108a and the circumferential wall 194 is configured to allow insertion of the outlet tube assembly 108a to a predetermined depth within the body 102a. The outlet tube assembly 108a may be placed in contact with and/or coupled to the circumferential wall 194. In some embodiments, the outlet tube assembly 108a may extend into and/or through the head cavity 190 and may be positioned against and/or coupled to the working head 4 of the powered hand-piece 2.

Figures 5A, 5B:
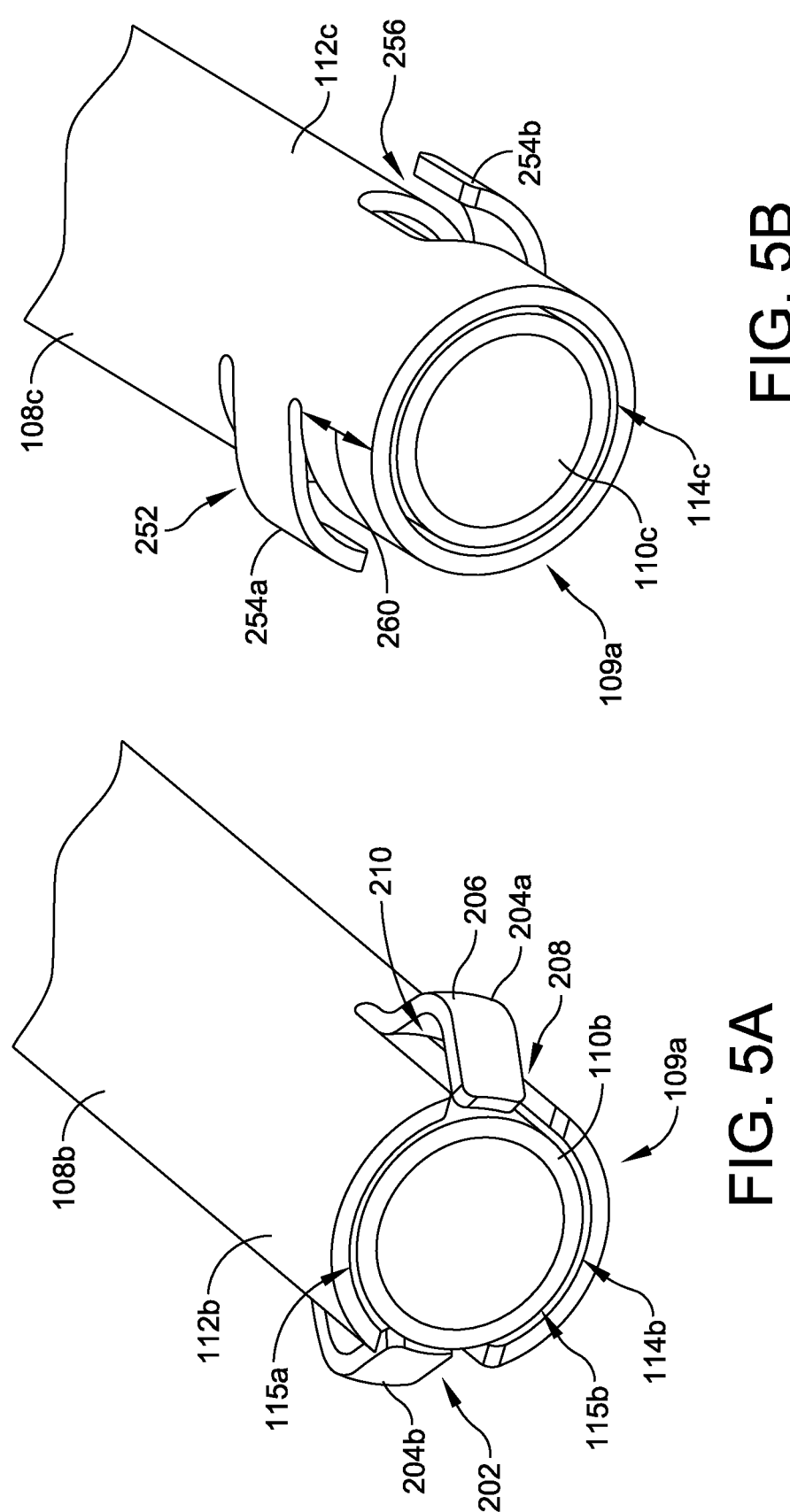
FIG. 5A illustrates a distal end of an outlet tube assembly having a first retention feature formed thereon, in accordance with some embodiments.
FIG. 5B illustrates a distal end of an outlet tube assembly having a second retention feature formed thereon, in accordance with some embodiments.

In some embodiments, the outlet tube assembly 108 may be configured to couple to and/or otherwise be retained at a surgical site. For example, FIG. 5A illustrates a distal end 109a of an outlet tube assembly 108b having a first retention feature 202 formed thereon, in accordance with some embodiments. The first retention feature 202 includes first and second spring clips 204a, 204b formed from the distal end 109a of the outlet tube assembly 108b. The spring clips 204a, 204b each include a bowed portion 206 extending out from the circumference of the outlet tube assembly 108b. The spring clips 204a, 204b are configured to be inserted into and compressed by an opening at a surgical site to maintain the outlet tube assembly 108b in a fixed proximal-distal position during operation of a tool.

The outlet tube assembly 108b includes a split fluid path 114b that includes an upper portion 115a and a lower portion 115b. The split fluid path 114b provides irrigation fluid substantially circumferentially about the working end of a tool 8 while providing for the bowed portions 206 to be formed in the distal end 109a of the outlet tube assembly 108b. In some embodiments, each of the spring clips 204a, 204b may expose a distal portion 208 of the split fluid path 114b. The distal portion 208 of the split fluid path 114b includes openings 210 formed by the spring clips 204a, 204b that allow irrigation fluid to exit the outlet tube assembly 108b proximal of the distal end 109a. In some embodiments, an additional tube or sealant (not shown) may be provided to prevent irrigation fluid from exiting the split fluid path 114b prior to the distal end 109a of the outlet tube assembly 108b.

As another example, FIG. 5B illustrates a distal end 109a of an outlet tube assembly 108c having a second retention feature 252 formed thereon, in accordance with some embodiments. The second retention feature 252 is similar to the first retention feature 202 and similar description is not repeated herein. The second retention feature 252 includes one or more spring clips 254a, 254b located proximally of the distal end 109a of the outlet tube assembly 108c. The spring clips 254a, 254b include tabs extending at a greater diameter than the remainder of the outlet tube assembly 108c. The spring clips 254a, 254b are configured to apply a frictional force at a surgical site to maintain the outlet tube assembly 108c in a fixed proximal-distal position.

In some embodiments, the outer tube 112c defines openings 256 at the location of the spring clips 254a, 254b that allows irrigation fluid to exit the outlet tube assembly 108c proximal to the distal end 109a. The distance 260 from the distal edge of the retention feature 252 to the distal end 109a of the outlet tube assembly 108c may be selected such that a fluid passing through fluid passage 114c has sufficient time to fill the circumferential passage 114c defined at the distal end 109a before exiting the outlet tube assembly 108c after passing the fluid openings 256.

Figure 6:
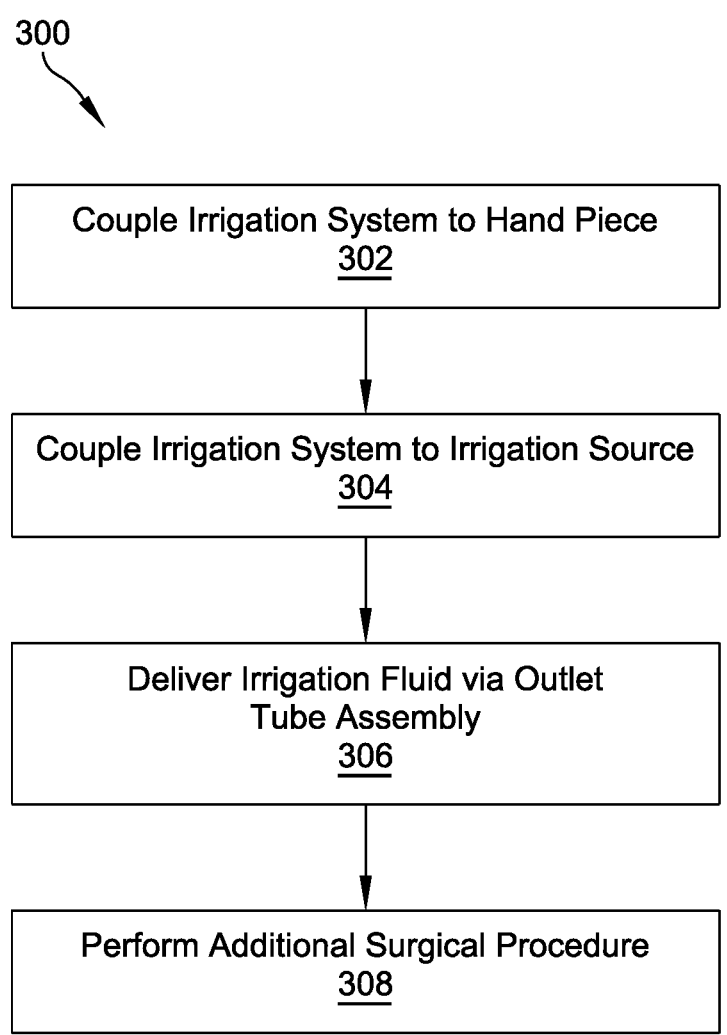
FIG. 6 is a flowchart illustrating a method, in accordance with some embodiments.
Figure 7:
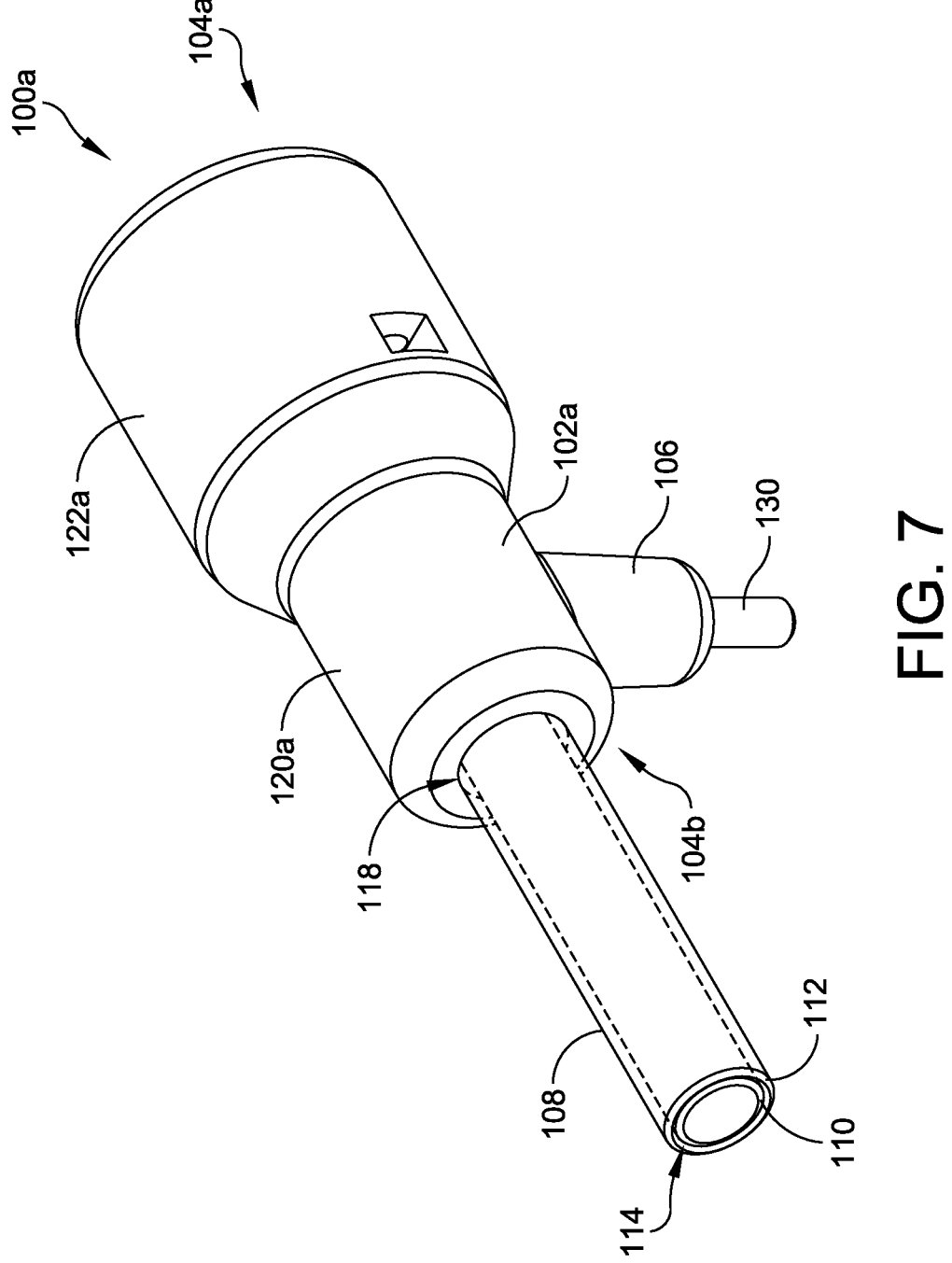
FIG. 7 illustrates an irrigation system including a pinwheel coupling element, in accordance with some embodiments.

FIG. 6 is a flowchart illustrating a method 300 of irrigating a working site using the irrigation system 100 described above, in accordance with some embodiments. With reference now to FIGS. 1-3 and 6, the method 300 is described. At step 302, an irrigation system 100 is coupled to the working end 4 of a powered hand-piece 2. The irrigation system 100 may be coupled to the powered hand-piece 2 by inserting the working end 4 into a head cavity 190 defined in a body 102 of the irrigation system 100. In some embodiments, the body 102 may be formed integrally with powered hand-piece 2.

At step 304, the irrigation system 100 is coupled to an irrigation source. An inlet 106 defining an internal passage 130 is coupled to, for example, an irrigation tube 10 extending from the irrigation source. The irrigation tube 10 may be coupled to the inlet 106 through a press-fit or sliding fit and/or using any other suitable mechanism. In some embodiments, the irrigation tube 10 is formed integrally with the inlet 106, for example, defining a portion of an inlet tube 130 extending through the inlet 106.

At step 306, a fluid, such as an irrigation fluid, is deliver to a working end of a tool 8 via a fluid path 114 defined by the irrigation system 100. For example, in some embodiments, an irrigation fluid is provided to the inlet 106 via the irrigation tube 10. The irrigation fluid flows through an inlet tube 130 defined by the inlet 106. In some embodiments, the irrigation fluid is provided to an inlet tube 130 defining the inlet tube 130. The irrigation fluid flows from the inlet tube 130 to the outlet tube assembly 108. The inlet tube 130 may be in fluid communication with the outlet tube assembly 108 via one or more internal chambers defined by the body 102 and/or may be directly coupled to the outlet tube assembly 108, as discussed above. The fluid proceeds through the fluid path 114 defined by the outlet tube assembly 108 and exits a distal end 109a of the outlet tube assembly 108 circumferentially about a working end of a tool 8. The irrigation fluid may be provided such that it interacts with the surgical site, the tool 8, and/or both simultaneously. The irrigation fluid may provide lubrication, medication delivery, cooling, debris removal, and/or any other suitable irrigation process.

At step 308, the tool 8 is removed from the working site and one or more additional surgical procedures are performed. In some embodiments, the irrigation system 100 may be transferred from the powered hand-piece 2 used to perform a first surgical procedure to a second hand-piece used to perform a second, or subsequent, surgical procedure. In other embodiments, the tool 8 may be disconnected from the powered hand-piece 2 and a second tool (not shown) may be coupled to the powered hand-piece without removing the irrigation system 100. Although specific embodiments are discussed herein, it will be appreciated that the irrigation system 100 may be used with any suitable hand-piece and/or any suitable tool configured to extend distally beyond the outlet tube assembly 108.

FIGS. 7-14 illustrate an irrigation system 100a including a pinwheel coupling element 400, in accordance with some embodiments. The irrigation system 100a is similar to the irrigation system 100 discussed above in conjunction with FIGS. 1-6, and similar description is not repeated herein. The irrigation system 100a includes a body 102a defining a head cavity 190a sized and configured to receive a portion of a tool, such as a portion of a drilling handpiece, therein. The head cavity 190a includes a pinwheel coupling element 400 configured to provide a press, or interference, fit with the portion of the tool inserted into the head cavity 190a.

The pinwheel coupling element 400 includes a plurality of interference fingers 402a-402c extending from an interior circumferential surface 404 of the head cavity 190a. In some embodiments, the interior circumferential surface 404 of the head cavity 190a is configured to provide a clearance fit with a portion of the tool inserted into the head cavity 190a. Each of the interference fingers 402a-402c extend at least partially into the head cavity 190a to define a contact surface configured to provide an interference fit with the portion of the tool inserted into the head cavity 190a. In some embodiments, the interior circumferential surface 404 comprises a solid, non-pliable material and each of the interference fingers 402a-402c comprise a pliable material configured to be at least partially deformed when a portion of a tool is inserted into the head cavity 190a. Contact with and deformation of the interference fingers 402a-402c provides a snug, interference retention of the tool within the head cavity 190a.

Figure 9:
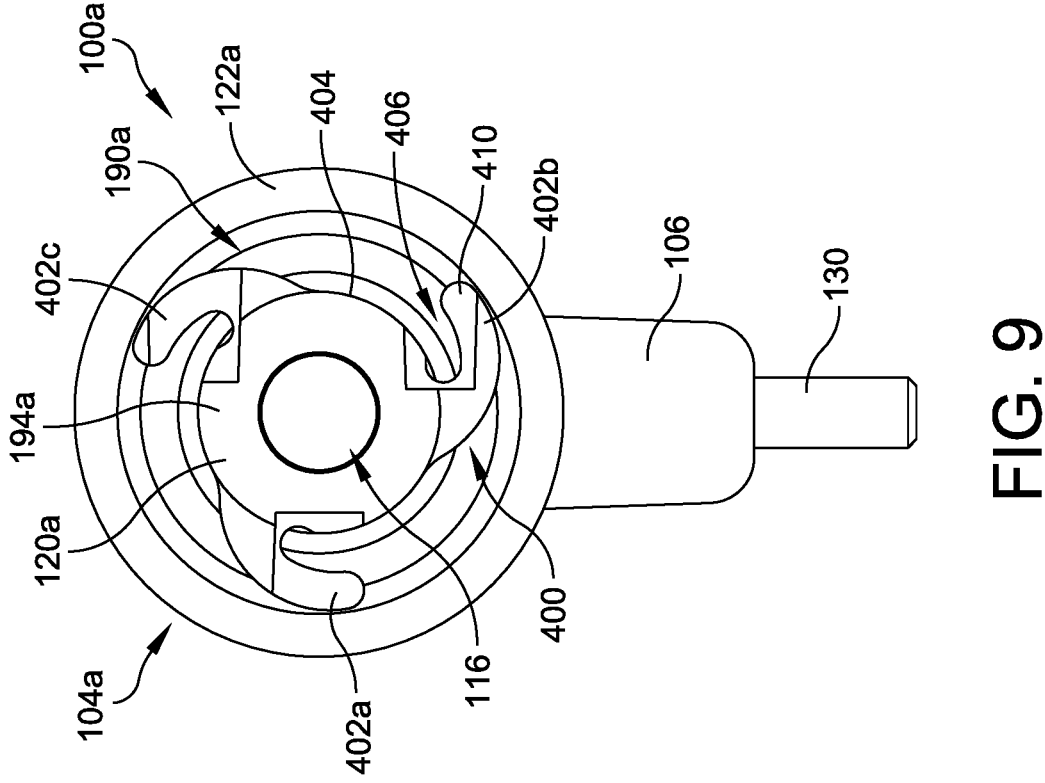
FIG. 9 illustrates a proximal view of the irrigation system of FIG. 7, in accordance with some embodiments.
Figure 8:
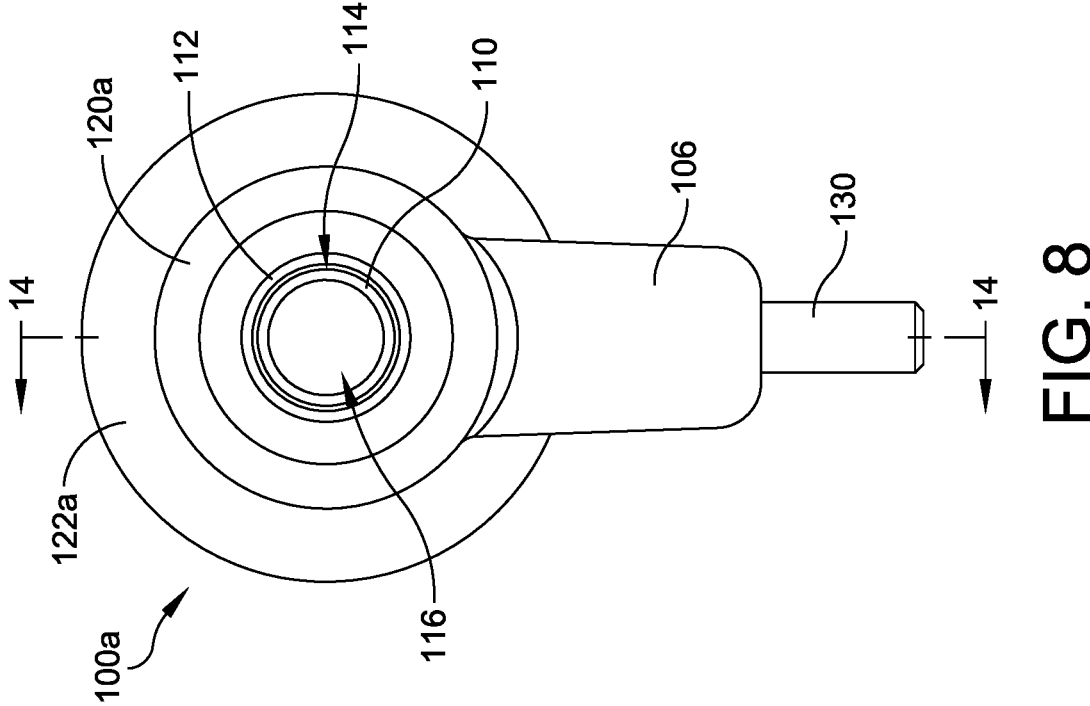
FIG. 8 illustrates a distal view of the irrigation system of FIG. 7, in accordance with some embodiments.
Figure 10:
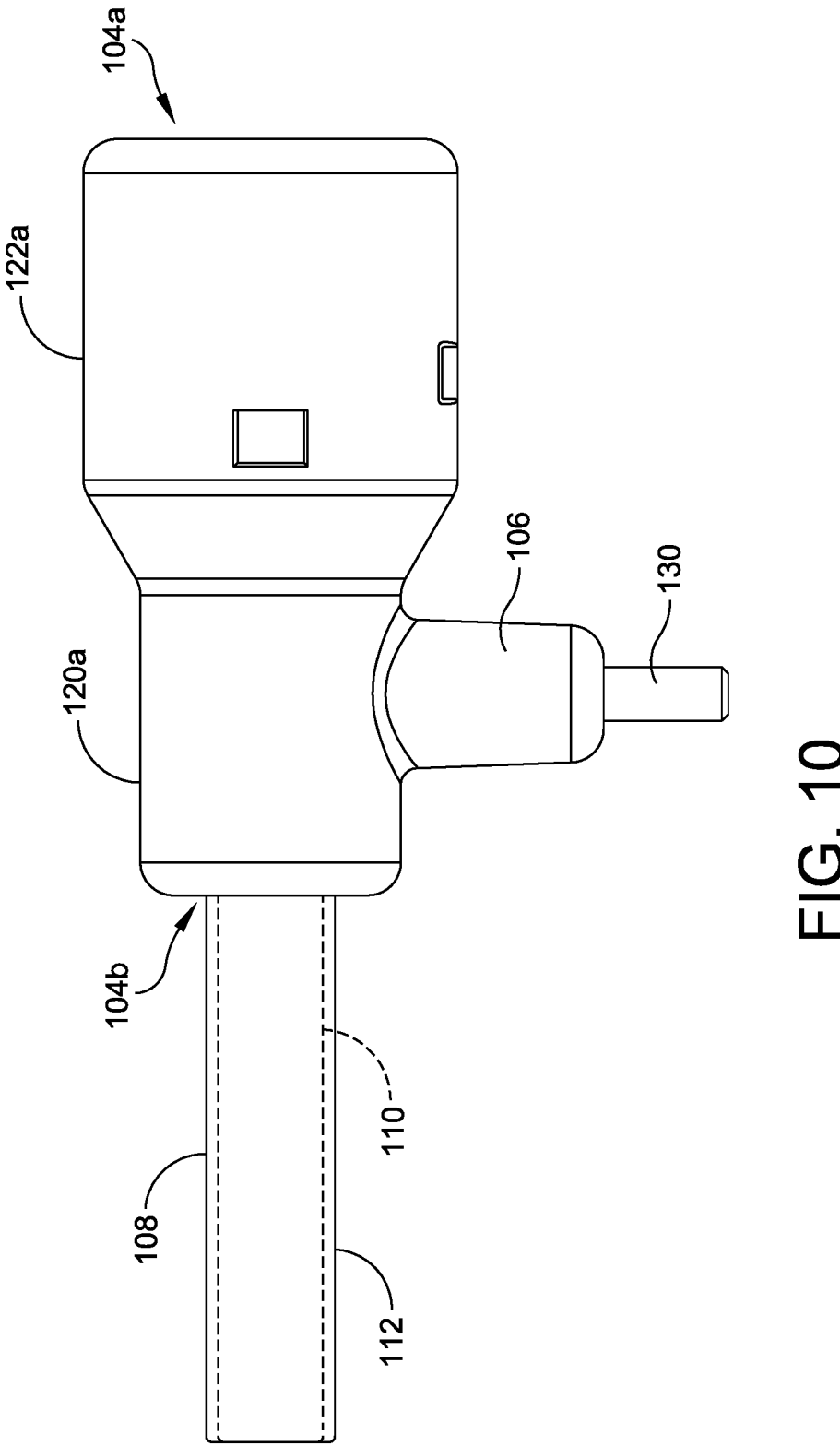
FIG. 10 illustrates a first side view of the irrigation system of FIG. 7, in accordance with some embodiments.
Figure 11:
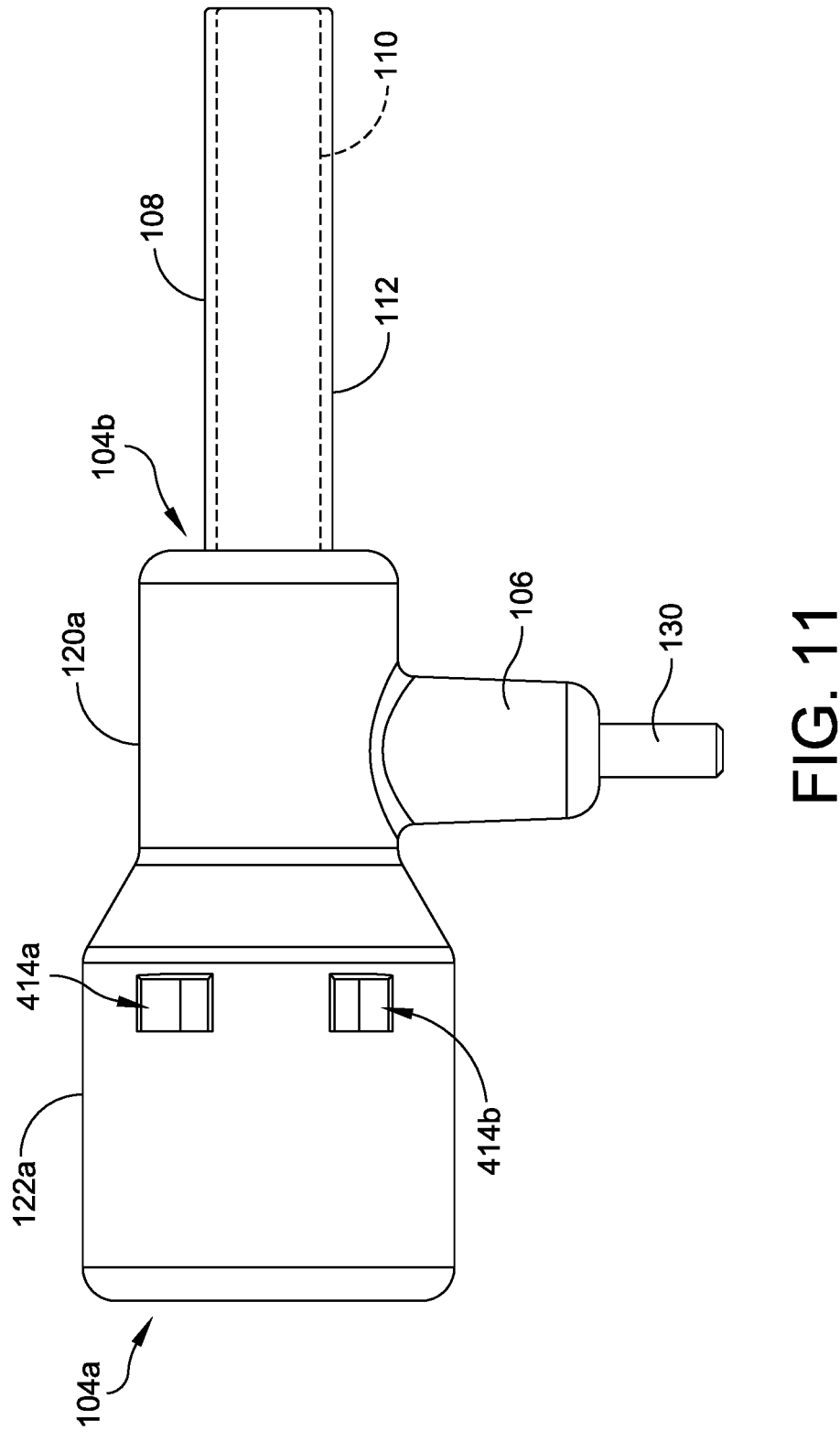
FIG. 11 illustrates a second side view of the irrigation system of FIG. 7, in accordance with some embodiments.
Figures 12, 13:
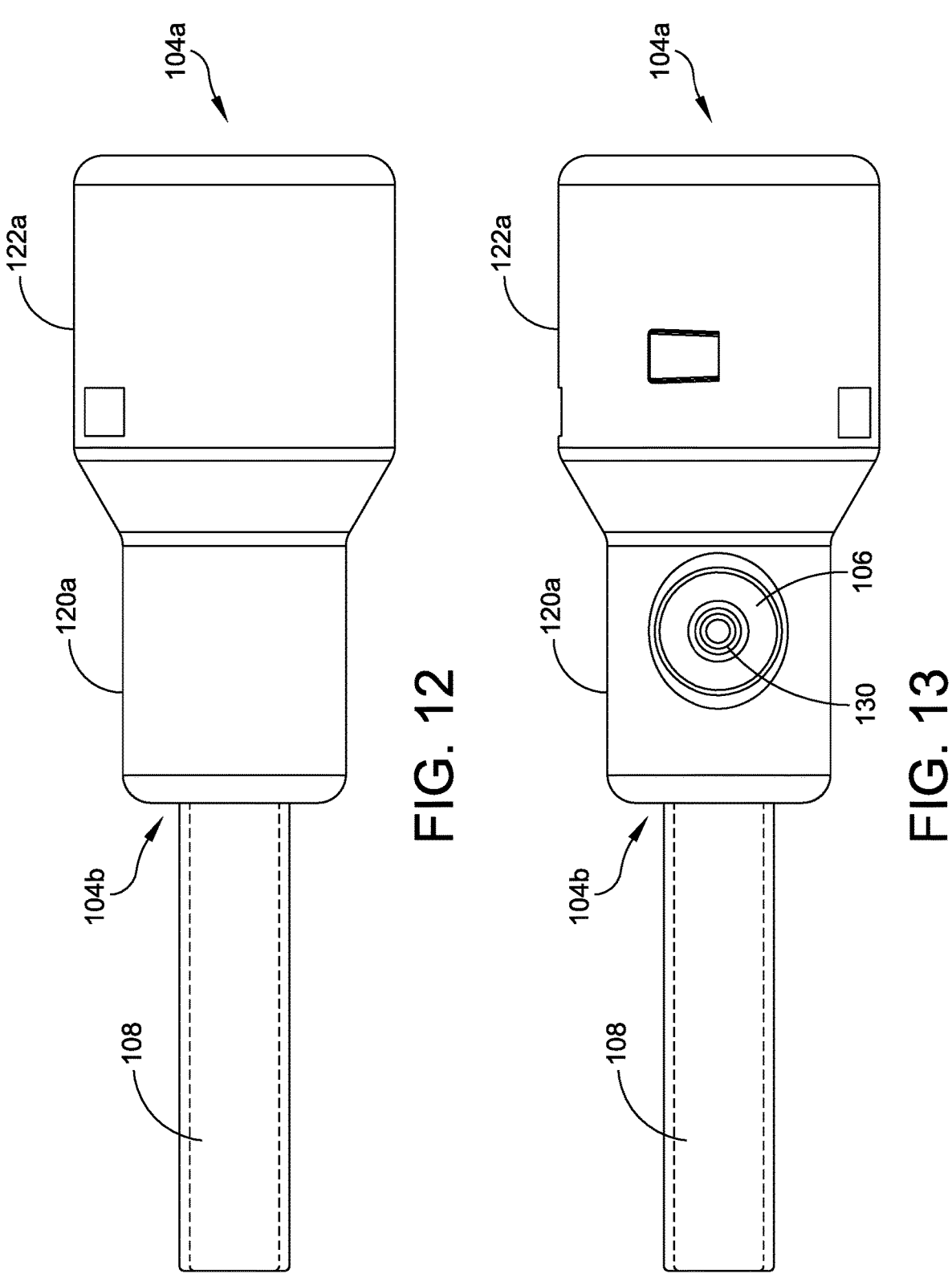
FIG. 12 illustrates a top view of the irrigation system of FIG. 7, in accordance with some embodiments.
FIG. 13 illustrates a bottom view of the irrigation system of FIG. 7, in accordance with some embodiments.
Figure 14:
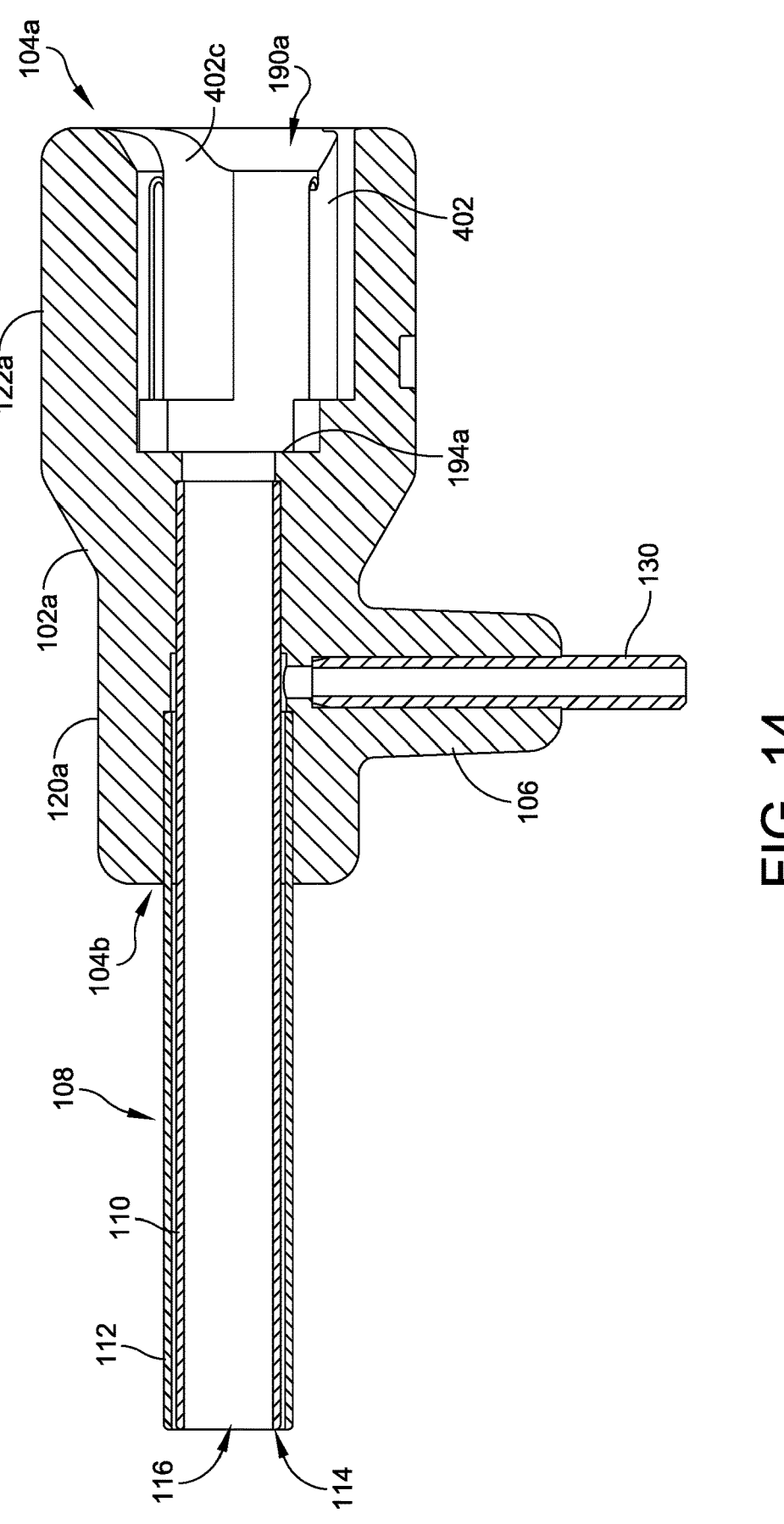
FIG. 14 illustrates cross-sectional view of the irrigation system of FIG. 7 taken along line 14-14 of FIG. 8, in accordance with some embodiments.
Figure 15:
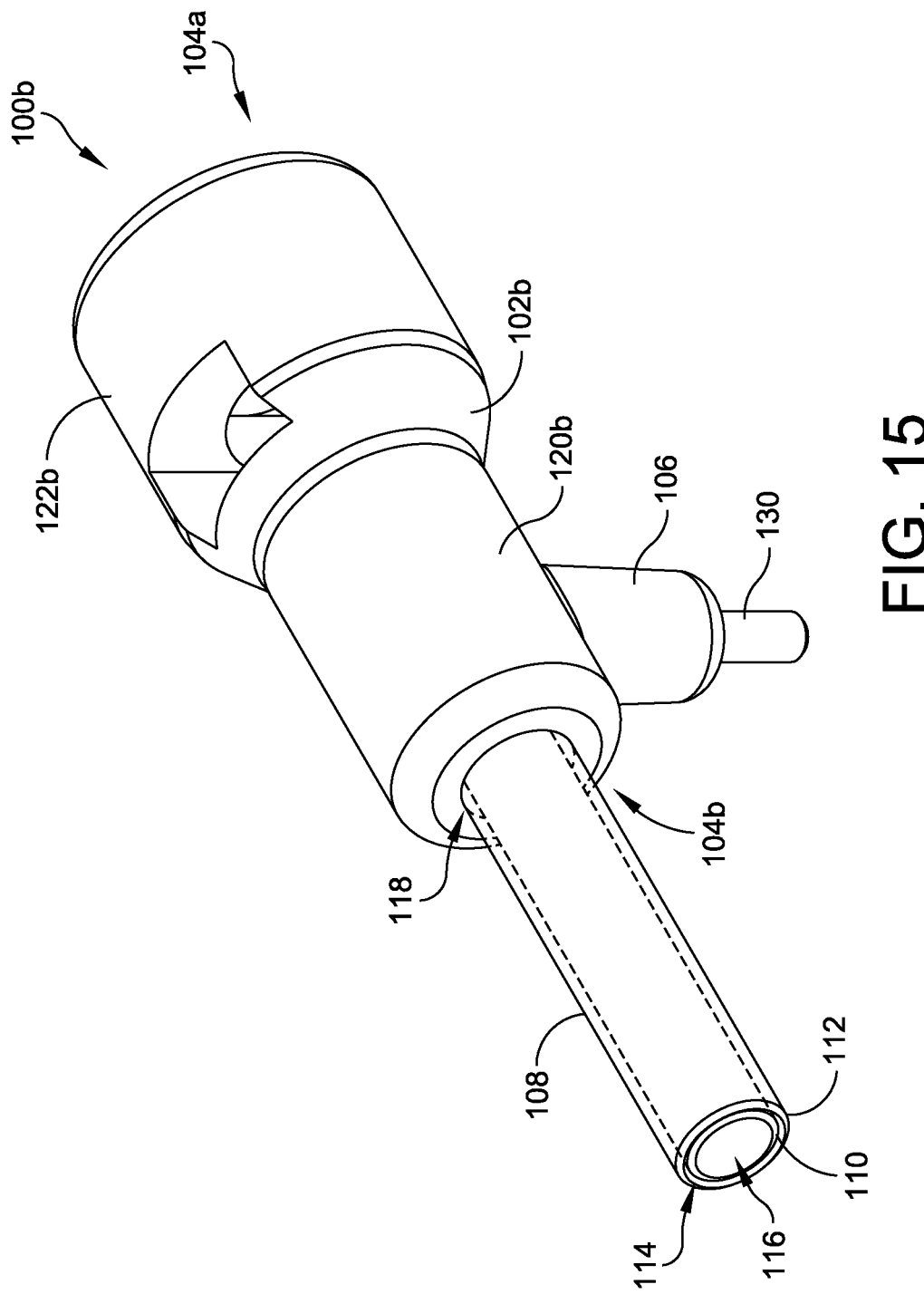
FIG. 15 illustrates an irrigation system including an interference bump coupling element, in accordance with some embodiments.
Figure 17:
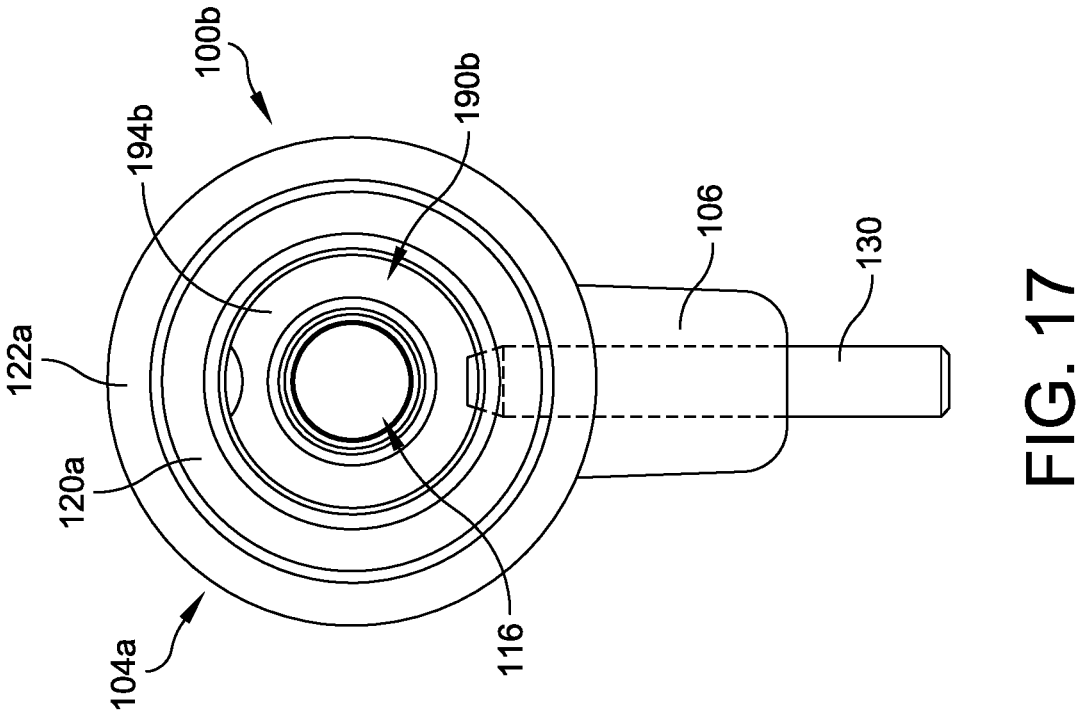
FIG. 17 illustrates a proximal view of the irrigation system of FIG. 15, in accordance with some embodiments.

In some embodiments, each of the interference fingers 402a-402c terminate prior to and/or spaced apart from an internal circumferential wall 194a defined by a proximal-most portion of the head cavity 190a, for example as shown in FIGS. 9 and 14. A gap 406, or spacing, is defined between the proximal ends 410 of each of the interference fingers 402a-402c and the internal circumferential wall 194a. In some embodiments, the gap 406 provides for consistent pliability of the interference fingers 402a-402c along the length of the interference fingers 402a-402c (e.g., along an axis extending from a distal end 412 to a proximal end 410 of the interference fingers 402a-402c). The gap 406 provides spacing for expansion and prevents bunching up of the interference fingers 402a-402c during insertion of the tool into the head cavity 190a. In some embodiments, one or more openings 412a, 412b are formed through a portion of the body 102a, such as a portion of the proximal body 122a. The openings 412a, 412b may be configured to provide expansion and/or force relief areas to allow for insertion of a tool without deformation of the head cavity 190a and/or the body 102a.

FIGS. 15-21 illustrate an irrigation system 100b including an interference bump coupling element 500, in accordance with some embodiments. The irrigation system 100b is similar to the irrigation systems 100, 100a discussed above in conjunction with FIGS. 1-14, and similar description is not repeated herein. The irrigation system 100b includes a body 102b defining a head cavity 190b sized and configured to receive a portion of a tool, such as a portion of a drilling handpiece, therein. The head cavity 190b includes an interference bump coupling element 500 configured to provide a press, or interference, fit with the portion of the tool inserted into the head cavity 190b.

The interference bump coupling element 500 includes at least one interference bump, or protrusion, extending from from an interior circumferential surface 504 of the head cavity 190b. In some embodiments, the interior circumferential surface 504 of the head cavity 190b is configured to provide a clearance fit with a portion of the tool inserted into the head cavity 190b. The at least one interference bump extends at least partially into the head cavity 190b to define a contact surface configured to provide an interference fit with the portion of the tool inserted into the head cavity 190b. In some embodiments, the interior circumferential surface 504 comprises a solid, non-pliable material and the interference bump 500 comprises a pliable material configured to be at least partially deformed when a portion of a tool is inserted into the head cavity 190b. Contact with and deformation of the interference bump 500 provides a snug, interference retention of the tool within the head cavity 190b.

Figure 16:
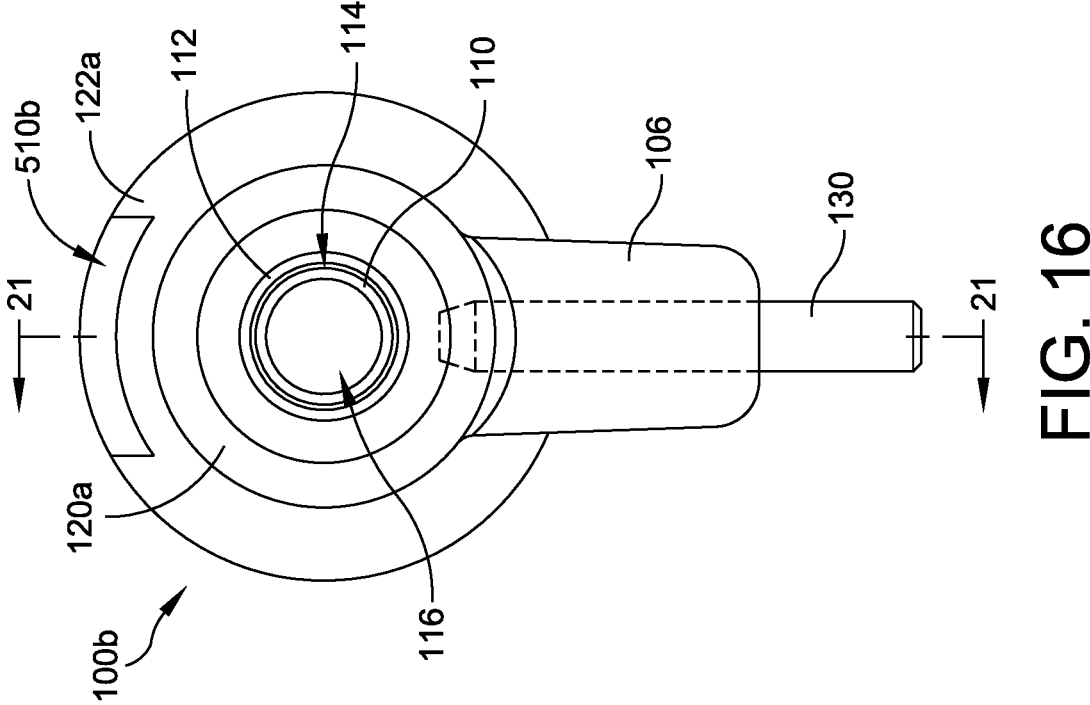
FIG. 16 illustrates a distal view of the irrigation system of FIG. 15, in accordance with some embodiments.
Figure 18:
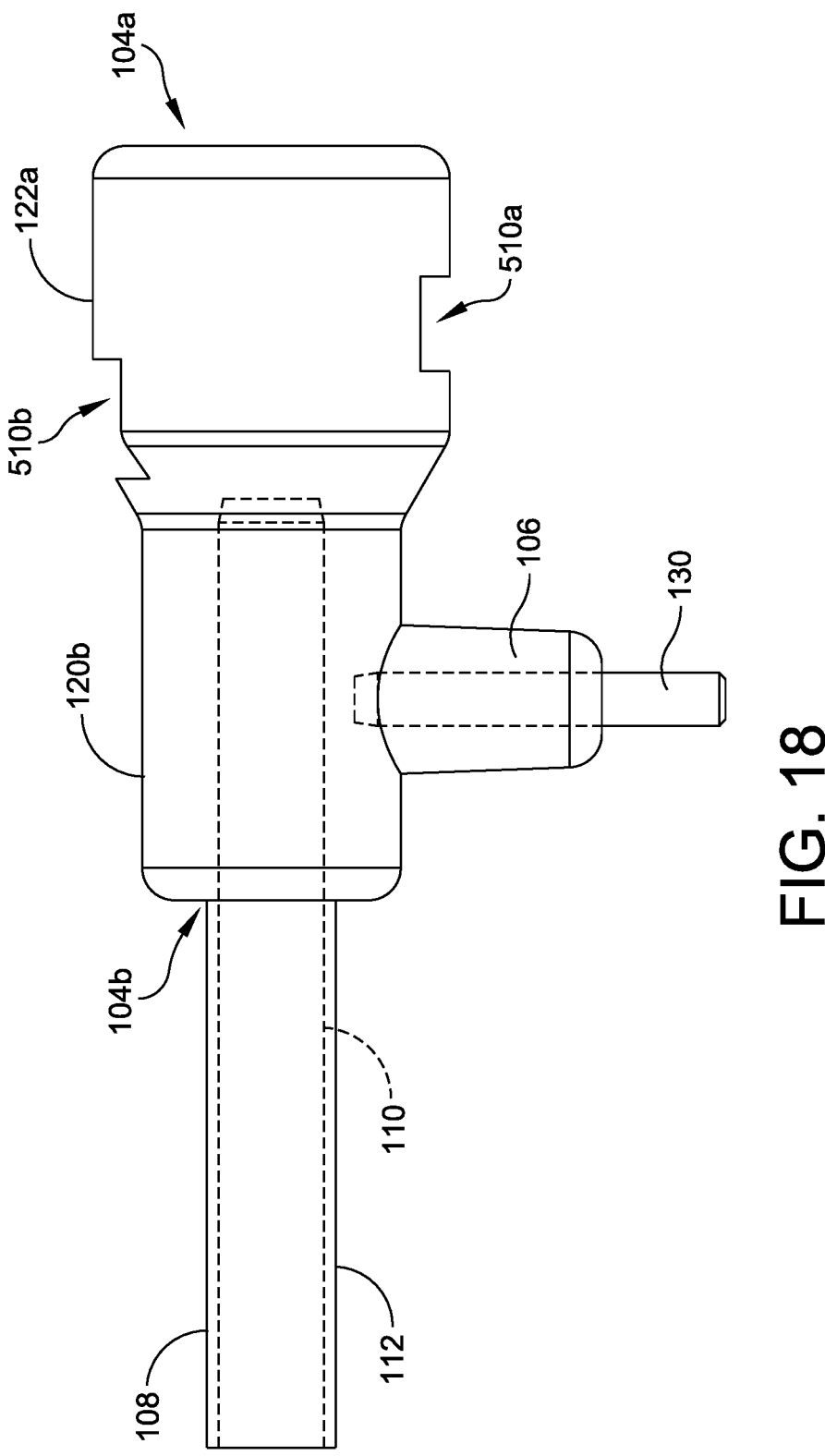
FIG. 18 illustrates a side view of the irrigation system of FIG. 15, in accordance with some embodiments.
Figures 19, 20:
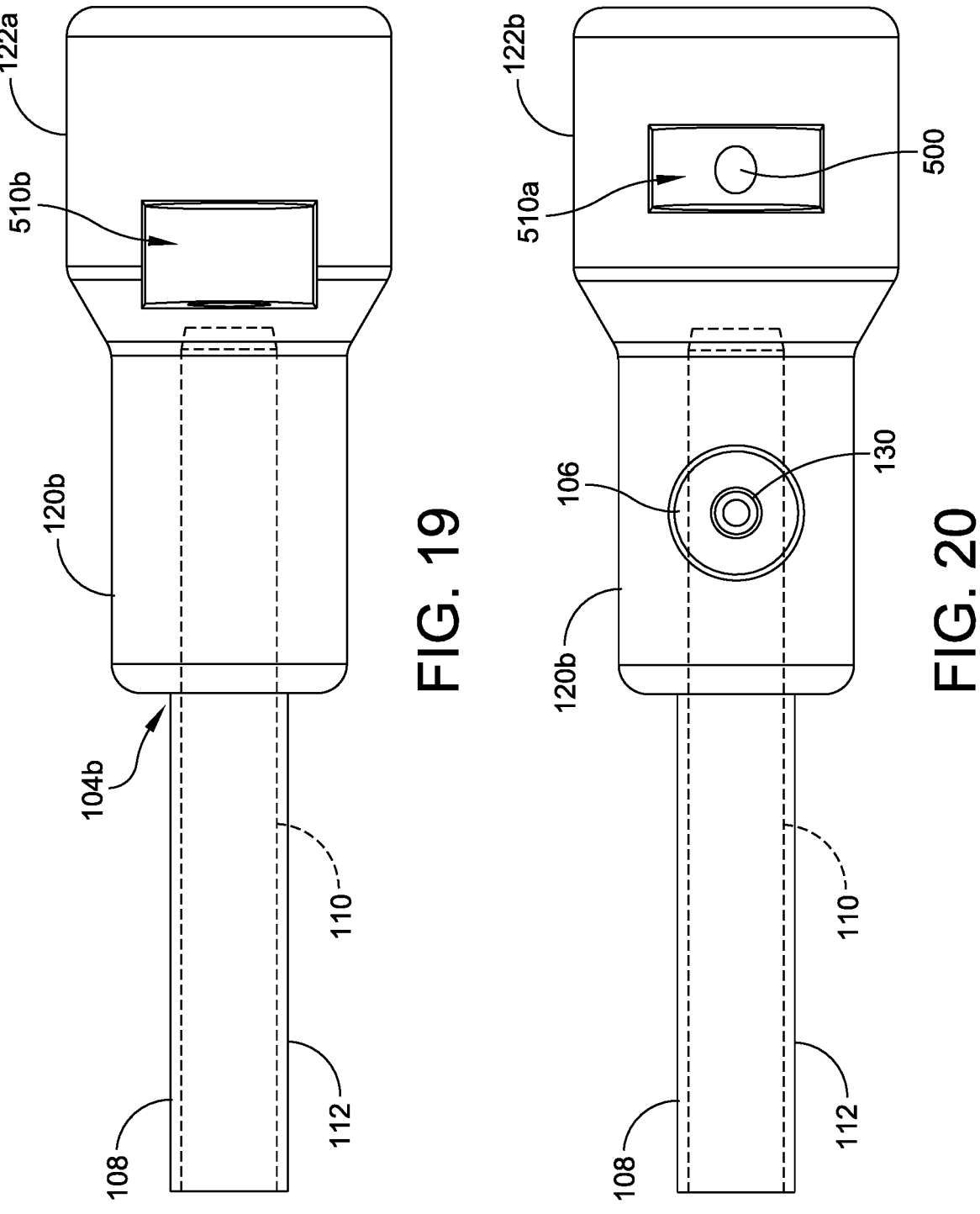
FIG. 19 illustrates a top view of the irrigation system of FIG. 15, in accordance with some embodiments.
FIG. 20 illustrates a bottom view of the irrigation system of FIG. 15, in accordance with some embodiments.
Figure 21:
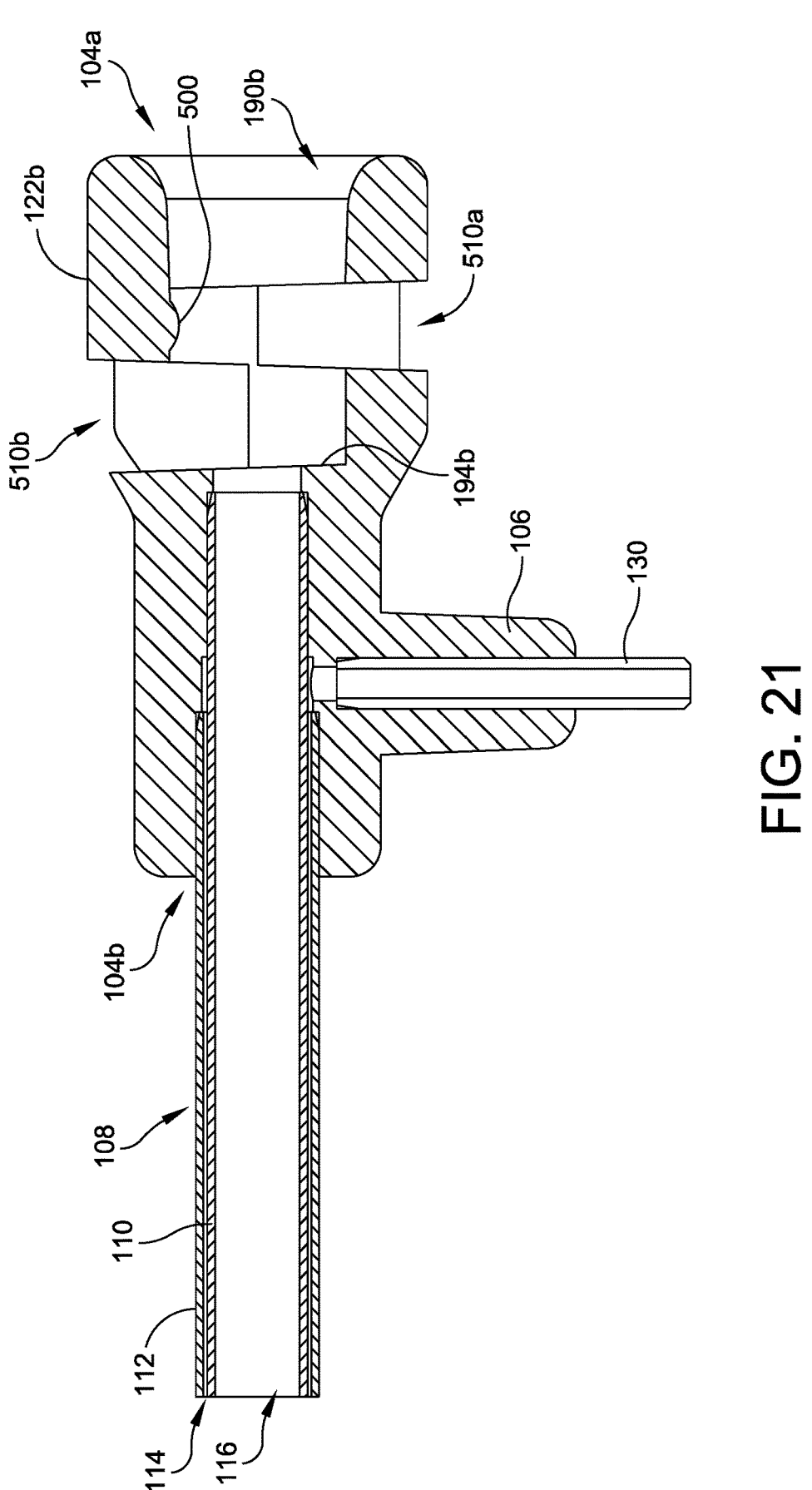
FIG. 21 illustrates cross-sectional view of the irrigation system of FIG. 15 taken along line 21-21 of FIG. 16, in accordance with some embodiments.

In some embodiments, the interference bump 502 is positioned at a middle, or center, point of the overall axial length of the head cavity 190b, as illustrated in FIGS. 16 and 21. Positioning of the interference bump 502 at a center point of the head cavity 190b provides supportive opposing points of contact for the portion of the tool inserted into the head cavity 190b on either side of the interference bump 502. By providing opposing points of contact, the irrigation system 100b can be maintained in a parallel relationship with the tool inserted at least partially into the head cavity 190b.

In some embodiments, one or more windows 510*a*, 510*b* are formed through a portion of the body 102*b*, such as a portion of the proximal body 122*b*. The windows 510*a*, 510*b* are configured to provide access to the head cavity 190*b*, for example, to a portion of a tool (not shown) inserted into the head cavity 190*b*. The windows 510*a*, 510*b* may be configured to provide access to adjustment mechanisms and/or other portions of a tool inserted into the head cavity 190*b*. In some embodiments, the windows 510*a*, 510*b* provide expansion and/or force relief areas to allow for insertion of a tool without deformation of the head cavity 190*b* and/or the body 102*b*.

Although the subject matter has been described in terms of exemplary embodiments, it is not limited thereto. Rather, the appended claims should be construed broadly, to include other variants and embodiments, which may be made by those skilled in the art.

What is claimed is:

1. A system, comprising:
   a body defining a proximal portion and a distal portion, wherein the proximal portion defines a cavity sized and configured to receive a working end of a hand-piece therein;
   an inlet tube extending through a portion of the body, the inlet tube configured to receive a fluid therethrough;
   an outlet tube assembly coupled to the distal portion of the body, wherein the outlet tube assembly extends distally beyond a distal edge of the body, wherein the outlet tube assembly comprises:
   an inner tube; and
   an outer tube, wherein the inner tube and the outer tube define a fluid path therebetween,
   wherein the inlet tube is in fluid communication with the outlet tube assembly such that when the fluid flows through the inlet tube and through the fluid path of the outlet tube assembly, the fluid exits the outlet tube assembly through an opening defined at a distal end, and
   wherein the outlet tube assembly comprises at least one retention feature having one or more spring clips configured to retain the outlet tube assembly at a surgical site, and further wherein each spring clip includes a bowed portion extending radially outwardly from the outlet tube assembly and the opening through which the fluid exits the outlet tube assembly at a location proximal to the distal end.

2. The system of claim 1, wherein the inlet tube and the outlet tube assembly are each in fluid communication with an internal cavity defined by the body, and wherein the internal cavity is configured to receive the fluid flow from the inlet tube and direct the fluid flow into the fluid path defined in the outlet tube assembly.

3. The system of claim 2, wherein the internal cavity is defined at least partially by an inner surface of the body and a surface of the inner tube of the outlet tube assembly.

4. The system of claim 1, wherein the body defines an internal passage having a stepped configuration comprising a plurality of circumferential sections.

5. The system of claim 4, wherein a diameter of each of the circumferential sections is different.

6. The system of claim 5, wherein the plurality of circumferential sections comprise:
   a first circumferential section defining a first diameter, wherein the first circumferential section extends from a proximal end of the body to a first position;

a second circumferential section defining a second diameter, wherein the second circumferential section extends from the first position to a second position;
   a third circumferential section defining a third diameter, wherein the third circumferential section extends from the second position to a third position; and
   a fourth circumferential section defining a fourth diameter, wherein the fourth circumferential section extends from the third position to a distal end of the body.

7. The system of claim 1, wherein the inner tube of the outlet tube assembly extends proximal to the outer tube of the outlet tube assembly.

8. The system of claim 1, wherein the inner tube is sealingly coupled to the outer tube.

9. A system, comprising:
   a powered hand-piece comprising a working end;
   a cutting tool operatively coupled to the working end of the powered hand-piece; and
   an irrigation system coupled to the working end of the powered hand-piece, the irrigation system comprising:
   a body defining a proximal portion and a distal portion, wherein the proximal portion defines a cavity sized and configured to receive the working end of the hand-piece therein, and wherein the distal portion defines a tool channel sized and configured to receive the cutting tool therethrough;
   an inlet tube extending through a portion of the body, the inlet tube configured to receive a fluid therethrough;
   an outlet tube assembly coupled to the distal portion of the body, wherein the outlet tube assembly extends at least partially through the tool channel, wherein the outlet tube assembly comprises:
   an inner tube; and
   an outer tube, wherein the inner tube and the outer tube define a fluid path therebetween,
   wherein the inlet tube is in fluid communication with the outlet tube assembly such that when the fluid flows through the inlet tube and through the fluid path of the outlet tube assembly, the fluid exits the outlet tube assembly through an opening spaced proximally from a distal end, wherein the opening of the outlet tube assembly is sized and arranged so that the fluid exits the opening circumferentially about the tool, and wherein the outlet tube assembly comprises at least one retention feature having one or more spring clips configured to retain the outlet tube assembly at a surgical site, each spring clip having a tab positioned outwardly from the remainder of the outlet tube assembly, the spring clip being positioned proximally of the distal end of the outlet tube assembly and located at the opening through which the fluid exits the outlet tube assembly.

10. The system of claim 9, wherein the inlet tube and the outlet tube assembly are each in fluid communication with an internal cavity defined by the body, wherein the internal cavity is configured to receive the fluid flow from the inlet tube and direct the fluid flow into the fluid path defined in the outlet tube assembly, and wherein the internal cavity defines a portion of the tool channel.

11. The system of claim 10, wherein the internal cavity is defined at least partially by an inner surface of the body and a surface of the inner tube of the outlet tube assembly.

12. The system of claim 9, wherein the tool channel comprises a stepped configuration including a plurality of circumferential sections.

13. The system of claim 12, wherein a diameter of each of the circumferential sections is different.

14. The system of claim 13, wherein the plurality of circumferential sections comprise:

a first circumferential section defining a first diameter, wherein the first circumferential section extends from a distal end of the body to a first position;

a second circumferential section defining a second diameter, wherein the second circumferential section extends from the first position to a second position; and a third circumferential section defining a third diameter, wherein the third circumferential section extends from the second position to a proximal end of the tool channel.

15. The system of claim 9, wherein the inner tube of the outlet tube assembly extends proximal to the outer tube of the outlet tube assembly.

16. The system of claim 9, wherein the inner tube is sealingly coupled to the outer tube.

17. A method, comprising:

coupling an irrigation system to a powered hand-piece, wherein the irrigation system comprises:

a body defining a proximal portion and a distal portion, wherein the proximal portion defines a cavity sized and configured to receive a working end of the hand-piece therein;

an inlet tube extending through a portion of the body;

an outlet tube assembly coupled to the distal portion of the body, wherein the outlet tube assembly extends at least partially through a tool channel, wherein the outlet tube assembly comprises:

an inner tube; and an outer tube, wherein the inner tube and the outer tube define a fluid path therebetween, wherein the inlet tube is in fluid communication with the outlet tube assembly, and wherein the outlet tube assembly comprises at least one retention feature having one or more spring clips configured to retain the outlet tube assembly at a surgical site, each spring clip having a tab positioned outwardly from the remainder of the outlet tube assembly, the spring clip being positioned proximally of a distal end of the outlet tube assembly and at an opening located proximally from the distal end of the outlet tube assembly through which a fluid exits the outlet tube assembly;

coupling a cutting tool to the powered hand-piece, wherein the cutting tool is received through the tool channel defined in the distal portion of the body;

providing the fluid to a distal end of the tool, so that when the fluid flows through the inlet tube and the outlet tube assembly, the opening of the outlet tube assembly provides the fluid circumferentially about the tool.

18. The method of claim 17, wherein the inlet tube and the outlet tube assembly are each in fluid communication with an internal cavity defined by the body, wherein the internal cavity is configured to receive the fluid from the inlet tube and direct the fluid into the fluid path defined in the outlet tube assembly, and wherein the internal cavity defines a portion of the tool channel.

* * * * *